US011990225B2

(12) United States Patent
Rodriguez

(10) Patent No.: US 11,990,225 B2
(45) Date of Patent: May 21, 2024

(54) SYSTEMS AND METHODS FOR RECONSTRUCTION OF MEDICAL IMAGES

(71) Applicant: Navix International Limited, Tortola (VG)

(72) Inventor: Haim Rodriguez, Tel-Mond (IL)

(73) Assignee: Navix International Limited, Road Town (VG)

( * ) Notice: Subject to any disclaimer, the term of this patent is extended or adjusted under 35 U.S.C. 154(b) by 675 days.

(21) Appl. No.: 17/256,024

(22) PCT Filed: Jul. 1, 2019

(86) PCT No.: PCT/IB2019/055567
§ 371 (c)(1),
(2) Date: Dec. 24, 2020

(87) PCT Pub. No.: WO2020/008326
PCT Pub. Date: Jan. 9, 2020

(65) Prior Publication Data
US 2021/0174940 A1 Jun. 10, 2021

Related U.S. Application Data

(60) Provisional application No. 62/693,919, filed on Jul. 4, 2018.

(51) Int. Cl.
*G16H 30/40* (2018.01)
*A61B 5/06* (2006.01)
*G06T 17/20* (2006.01)

(52) U.S. Cl.
CPC ............ *G16H 30/40* (2018.01); *A61B 5/065* (2013.01); *G06T 17/20* (2013.01); *A61B 2576/023* (2013.01); *G06T 2210/41* (2013.01)

(58) Field of Classification Search
CPC .. G16H 30/40; A61B 5/065; A61B 2576/023; A61B 5/7278; A61B 2576/026;
(Continued)

(56) References Cited

U.S. PATENT DOCUMENTS 7,263,397 B2 * 8/2007 Hauck .................... A61B 5/065
600/509
2011/0092808 A1 4/2011 Shachar et al.
(Continued)

FOREIGN PATENT DOCUMENTS

| WO | WO-2007084647 A2 * | 7/2007 | ............... A61B 1/24 |
| WO | WO 2020/008326 | 1/2020 | |
| WO | WO 2020/008326 A9 | 1/2020 | |

OTHER PUBLICATIONS

Liang et al. 2013 J. Sci. Comput. 54:577-602 (Year: 2013).*
(Continued)

*Primary Examiner* — Keith M Raymond
*Assistant Examiner* — Patrick M Mehl

(57) ABSTRACT

There is provided a computer implemented method of reconstructing an image of a body cavity shape of a subject based on a plurality of location indications, indicating locations of at least one sensor disposed on an intrabody probe within the body cavity, the method comprising: receiving data indicative of the plurality of location indications, identifying based on the data at least a first group and a second group of location indications, and reconstructing the body cavity from the data, using a first reconstruction method for the first group of location indications, and a second reconstruction method for the second group of location indications.

8 Claims, 12 Drawing Sheets

(58) Field of Classification Search
CPC ....... A61B 5/06; A61B 5/1073; A61B 5/6852; A61B 5/0044; G06T 17/20; G06T 2210/41

See application file for complete search history.

(56) References Cited

U.S. PATENT DOCUMENTS

| | | | |
|---|---|---|---|
| 2013/0138404 A1* | 5/2013 | Carbonera | G06T 17/205 703/2 |
| 2013/0173222 A1 | 7/2013 | Voth | |
| 2015/0164356 A1* | 6/2015 | Merschon | A61B 5/6852 600/374 |
| 2017/0330487 A1* | 11/2017 | Harlev | G16H 15/00 |

OTHER PUBLICATIONS

Zhou et al. 2012 IEEE International Conference on Audio Language and Image Processing Shanghai pp. 1098-1103 (Year: 2012).*

International Preliminary Report on Patentability Dated Jan. 10, 2021 From the International Bureau of WIPO Re. Application No. PCT/IB2019/055567. (10 Pages).

International Search Report and the Written Opinion Dated Sep. 18, 2019 From the International Searching Authority Re. Application No. PCT/IB2019/055567. (19 Pages).

Chiang et al. "Progressive Surface Reconstruction for Heart Mapping Procedure", Computer-Aided Design, XP028450900, 44(4): 289-299, Apr. 2012.

* cited by examiner

SYSTEMS AND METHODS FOR RECONSTRUCTION OF MEDICAL IMAGES

RELATED APPLICATIONS

This application is a National Phase of PCT Patent Application No. PCT/IB2019/055567 having International filing date of Jul. 1, 2019, which claims the benefit of priority under 35 USC § 119(e) of U.S. Provisional Patent Application No. 62/693,919 filed on Jul. 4, 2018. The contents of the above applications are all incorporated by reference as if fully set forth herein in their entirety.

BACKGROUND

The present invention, in some embodiments thereof, relates to medical imaging and, more specifically, but not exclusively, to systems and methods for reconstruction of a body cavity image.

Several medical procedures in cardiology and other medical fields comprise the use of intrabody probes such as catheter probes to reach tissue targeted for diagnosis and/or treatment while minimizing procedure invasiveness. Early imaging-based techniques (such as fluoroscopy) for navigation of the catheter and monitoring of treatments continue to be refined, and are now joined by techniques such as electromagnetic field-guided position sensing systems.

SUMMARY

According to a first aspect, a computer implemented method of reconstructing an image of a body cavity shape of a subject based on a plurality of location indications, indicating locations of at least one sensor disposed on an intrabody probe within the body cavity, the method comprises: receiving data indicative of the plurality of location indications, identifying based on the data at least a first group and a second group of location indications, and reconstructing the body cavity from the data, using a first reconstruction method for the first group of location indications, and a second reconstruction method for the second group of location indications.

According to a second aspect, a system for reconstructing a body cavity shape of a subject based on a plurality of location indications indicating locations of at least one sensor disposed on an intrabody probe within the body cavity, comprises: a non-transitory memory having stored thereon a code for execution by at least one hardware processor, the code comprising: code for receiving data indicative of the plurality of location indications, code for identifying based on the data at least a first group and a second group of location indications, and code for reconstructing the body cavity from the data, using a first reconstruction process for the first group of location indications, and a second reconstruction process for the second group of location indications.

According to a third aspect, a computer implemented method of reconstructing an image of a body cavity shape of a subject based on a point cloud, each point representing a location visited by an intra body probe, the point cloud having an inner region wherein the points are sparser than outside said inner region of the point cloud, the method comprises: identifying the inner region, adding points to the inner region of the cloud to emulate additional visits of the intrabody probe in said inner region, and reconstructing the image of the body cavity shape from the point cloud after the adding.

According to a fourth aspect, a system for reconstructing an image of a body cavity shape of a subject based on a point cloud, in which each point represents a location visited by an intra body probe, the point cloud having an inner region wherein the points are sparser than outside said inner region, the system comprising a non-transitory memory having stored thereon a code for execution by at least one hardware processor, the code comprises: code to add points to the inner region of the cloud to emulate additional visits of the intrabody probe in said inner region, and code to reconstruct the image of the body cavity shape from the point cloud after the adding.

According to a fifth aspect, a computer implemented method of reconstructing an image of a body cavity shape of a subject based on a plurality of location indications indicating locations of at least one sensor disposed on an intrabody probe within the body cavity, the method comprises: receiving the plurality of location indications of the at least one sensor disposed on the intrabody probe with the body cavity, uniformly sampling the plurality of location indications, computing a point density function (PDF) based on the uniformly sampled plurality of location indications, computing a contour function by subtracting a threshold from the computed PDF, and reconstructing an image of an outer shell of the body cavity according to the contour function.

According to a sixth aspect, a system for reconstructing a body cavity shape of a subject based on a plurality of location indications of at least one sensor disposed on an intrabody probe within the body cavity, comprises: a non-transitory memory having stored thereon a code for execution by at least one hardware processor, the code comprising: code for receiving the plurality of location indications of the at least one sensor disposed on the intrabody probe with the body cavity, code for uniformly sampling the plurality of location indications, code for computing a point density function (PDF) based on the uniformly sampled plurality of location indications, code for computing a contour function by subtracting a predetermined threshold from the computed PDF, and code for reconstructing an image of an outer shell of the body cavity according to the contour function.

According to a seventh aspect, computer program product for reconstructing a body cavity shape of a subject based on a plurality of location indications of at least one sensor disposed on an intrabody probe within the body cavity, comprises: a non-transitory memory having stored thereon a code for execution by at least one hardware processor, the code comprising: instructions for receiving the plurality of location indications of the at least one sensor disposed on the intrabody probe with the body cavity, instructions for uniformly sampling the plurality of location indications, instructions for computing a point density function (PDF) based on the uniformly sampled plurality of location indications, instructions for computing a contour function by subtracting a predetermined threshold from the computed PDF, and instructions for reconstructing an image of an outer shell of the body cavity according to the contour function.

In a further implementation of the first aspect, the locations indicated by the location indications of each group are in a different region of the body cavity.

In a further implementation of the first aspect, the locations indicated by the location indications of the first group are closer to the outer shell of the body cavity than the locations indicated by the location indications of the second group.

In a further implementation of the first aspect, the identifying of the first and second group of location indications is according to proximity of the indicated locations to an outer shell of the body cavity.

In a further implementation of the first aspect, each of the first and second reconstruction methods include uniformly sampling the data in the corresponding group.

In a further implementation of the first aspect, one of the reconstruction methods is different from the other in a sampling rate of the uniform sampling.

In a further implementation of the first aspect, each of the first and second reconstruction methods comprise setting a threshold to a point density function (PDF) describing the density of the location indications in the corresponding group, and the two methods differ in the value of the threshold.

In a further implementation of the first aspect, each of the point density functions describe the density of a uniform sample of location indications.

In a further implementation of the first aspect, at least one of the first and second reconstruction methods comprises computing a non-zero number of emulated location indications that represent a non-visited location of the at least one sensor.

In a further implementation of the first aspect, the first group includes no emulated location indications or fewer emulated location indications than the second group.

In a further implementation of the second aspect, the code to identify the first and second group of location indications is to identify the groups according to proximity of the indicated locations to an outer shell of the body cavity.

In a further implementation of the second aspect, each of the first and second reconstruction processes include uniformly sampling the data in the corresponding group.

In a further implementation of the second aspect, one of the reconstruction processes is different from the other in a sampling rate of the uniform sampling.

In a further implementation of the second aspect, each of the first and second reconstruction processes comprise setting a threshold to a point density function (PDF) describing the density of the location indications in the corresponding group, and the two processes differ in the value of the threshold.

In a further implementation of the second aspect, each of the point density functions describe the density of a uniform sample of location indications.

In a further implementation of the second aspect, at least one of the first and second reconstruction processes comprises computing a non-zero number of emulated location indications that represent a non-visited location of the at least one sensor.

In a further implementation of the second aspect, the first group includes no emulated location indications or fewer emulated location indications than the second group.

In a further implementation of the third aspect, further comprises uniformly sampling the points in the point cloud, and said adding points is carried out after said uniformly sampling.

In a further implementation of the third aspect, said reconstructing is based on a contour function generated by: computing a point density function (PDF) based on the uniformly sampled point cloud, and computing the contour function by subtracting a predetermined threshold from the computed PDF.

In a further implementation of the third aspect, said reconstructing comprises reconstructing an outer shell of the shape according to locations wherein the contour function borders between positive and negative values.

In a further implementation of the third aspect, said reconstructing comprises reconstructing an outer shell of the shape from the contour function according to a marching cube computational process.

In a further implementation of the third aspect, comprising identifying the inner region as a region lying a predefined distance away from an estimated location of an inner wall of the body cavity.

In a further implementation of the fourth aspect, the instructions further comprise code for uniformly sampling the points in the point cloud, and said code for adding points is executed after said uniformly sampling.

In a further implementation of the fourth aspect, said code to reconstruct the image comprises code to evaluate a contour function generated by: computing a point density function (PDF) based on the uniformly sampled point cloud, and computing the contour function by subtracting a predetermined threshold from the computed PDF.

In a further implementation of the fourth aspect, said code for reconstructing comprises code for reconstructing an outer shell of the shape according to locations wherein the contour function borders between positive and negative values.

In a further implementation of the fourth aspect, said code for reconstructing comprises code for reconstructing an outer shell of the shape from the contour function according to a marching cube computational process.

In a further implementation of the fourth aspect, the instructions further comprise code for identifying the inner region as a region lying a predefined distance away from an estimated location of an inner wall of the body cavity.

In a further implementation of the fifth, sixth, and seventh aspect, the plurality of location indications comprise a point cloud obtained by maneuvering of the intrabody probe to various spatial locations within a three dimensional (3D) space within the body cavity.

In a further implementation of the fifth, sixth, and seventh aspect, the uniformly sampling of the plurality of location indications comprises assigning an equal value to each grid cell comprising at least one location indication independent of density and/or number of location indications within the respective grid cell.

In a further implementation of the fifth, sixth, and seventh aspect, a first group of the plurality of location indications obtained within at least one first region of the body cavity are arranged at a first density, and a second group of the plurality of location indications obtained within at least one second region of the body cavity are arranged at a second density that is lower than the first density, and wherein the uniformly sampling is performed at a same rate for the first and second groups.

In a further implementation of the fifth, sixth, and seventh aspect, the uniform sampling is performed by computing a 3D grid having uniform cell size that includes the location indications, selecting a single location indication for each cell that includes two or more location indications and discarding non-selected location indications.

In a further implementation of the fifth, sixth, and seventh aspect, the PDF is computed from the cells of the 3D grid that include location indications and ignoring cells of the 3D grid without location indications.

In a further implementation of the fifth, sixth, and seventh aspect, the PDF is computed by computing a plurality of distribution functions each centered at the location indication corresponding to a corresponding one of the uniformly sampled plurality of location indications, and computing for each respective point of the 3D grid a sum of the value of all the plurality of distribution functions.

In a further implementation of the fifth, sixth, and seventh aspect, the plurality of distribution functions are selected from the group consisting of: Gaussian, and cosine.

In a further implementation of the fifth, sixth, and seventh aspect, the PDF is computed using a nonparametric kernel process.

In a further implementation of the fifth, sixth, and seventh aspect, the outer shell of the body cavity is reconstructed according to the contour function by selecting portions of the contour function that border between positive and negative values.

In a further implementation of the fifth, sixth, and seventh aspect, the value of the threshold is computed by trial and error of multiple iterations using different values to select a certain value that results in a reconstruction in which target detailed structures are most delineated and visible.

In a further implementation of the fifth, sixth, and seventh aspect, the threshold is selected to define between a first group of locations located externally to an inner wall of the body cavity, and a second group of locations associated located within an interior of the body cavity bounded by the inner wall of the body cavity.

In a further implementation of the fifth, sixth, and seventh aspect, locations associated with values of the contour function indicating locations external to the inner wall of the body cavity are excluded from the image of the outer shell.

In a further implementation of the fifth, sixth, and seventh aspect, the outer shell is reconstructed from the contour function according to a marching cube computational process.

In a further implementation of the fifth, sixth, and seventh aspect, further comprising: providing at least one marking indicative of a location of the body cavity where a medical procedure is performed, and reconstructing the image of the outer shell of the body cavity according to the contour function and the at least one marking.

In a further implementation of the fifth, sixth, and seventh aspect, the reconstructing comprises computing a mesh denoting the outer shell so that the mesh intersects each of the at least one marking while maintaining each at least one marking in its original location.

In a further implementation of the fifth, sixth, and seventh aspect, markings having the original actual location greater than a predefined outlier distance from the mesh are excluded from the image of the outer shell.

In a further implementation of the fifth, sixth, and seventh aspect, each at least one marking is denoted by at least one of the plurality of location indications.

In a further implementation of the fifth, sixth, and seventh aspect, further comprising: selecting at least one region within the uniformly sampled plurality of location indications, computing a set of emulated location indications within the at least one region, uniformly sampling the set of emulated location indications and uniformly sampling non-emulated plurality of location indications, wherein the PDF is computed based on the uniformly sampled plurality of non-emulated location indications and the uniformly sampled set of emulated location indications.

In a further implementation of the fifth, sixth, and seventh aspect, the at least one region is selected according to a prediction of a plurality of cells of a 3D grid lacking location indications, wherein the 3D grid is used for sampling the plurality of location indications to compute the uniformly sampled plurality of location indications.

In a further implementation of the fifth, sixth, and seventh aspect, the at least one region is located within the interior of the body cavity, away from an inner wall of the body cavity.

In a further implementation of the fifth, sixth, and seventh aspect, selecting the at least one region comprises computing the at least one region according to a predefined distance away from an estimated location indication of an inner wall of the body cavity.

In a further implementation of the fifth, sixth, and seventh aspect, the predefined distance is computed based on a Mahalanobis distance from a computed center of mass of the uniformly sampled plurality of location indications, less than a predefined distance threshold.

In a further implementation of the fifth, sixth, and seventh aspect, computing the set of emulated location indications comprises: computing a second PDF for the selected at least one region, computing a second 3D grid of cells for the selected at least one region, and computing at least one emulated location indication for each cell of the 3D grid, wherein a value of the second PDF corresponding to the respective cell is below a second threshold.

In a further implementation of the fifth, sixth, and seventh aspect, the second threshold is lower than the predefined threshold subtracted from the PDF to compute the contour function.

In a further implementation of the fifth, sixth, and seventh aspect, the body cavity comprises the left atrium, and wherein the selecting the at least one region comprises: identifying a first region with Mahalanobis distances from a center of mass of the uniformly sampled plurality of location indications less than a predefined distance threshold.

In a further implementation of the fifth, sixth, and seventh aspect, the identifying of the at least one region further comprises: identifying a second region according to a set of rules different than the Mahalanobis distances for identifying the first region, unifying the first region and the second region to create the at least one region.

In a further implementation of the fifth, sixth, and seventh aspect, a non-height dimension of the second region is the same as a corresponding non-height dimension of the first region.

In a further implementation of the fifth, sixth, and seventh aspect, a lower border of the second region is according to a predefined height above a bottom of the plurality of location indications within the body cavity.

In a further implementation of the fifth, sixth, and seventh aspect, an upper border of the second region penetrates the first region.

In a further implementation of the fifth, sixth, and seventh aspect, the penetration of the first region by the second region is according to a predefined portion of location indications of the first region.

In a further implementation of the fifth, sixth, and seventh aspect, the predefined portion of location indications of the first region is a predefined percentage of the location indications of the first region.

In a further implementation of the fifth, sixth, and seventh aspect, the predefined distance threshold is about 1.1.

In a further implementation of the fifth, sixth, and seventh aspect, further comprising presenting the reconstructed image of the outer shell of the body cavity on a display.

In a further implementation of the fifth, sixth, and seventh aspect, the plurality of location indications are computed based on a plurality of electrical readings, magnetic readings, or transformations thereof, made by the at least one sensor disposed on the intrabody probe.

According to an eighth aspect, a computer implemented method of reconstructing an image of a body cavity shape of a subject based on a plurality of location indications of at least one sensor disposed on an intrabody probe within the body cavity, comprises: receiving data indicative of the plurality of location indications of the at least one sensor disposed on the intrabody probe with the body cavity, identifying based on the data at least a first group and a second group of location indications, and reconstructing the body cavity from the data, using a first reconstruction method for the first group of location indications, and a second reconstruction method for the second group of location indications.

According to a ninth aspect, a system for reconstructing a body cavity shape of a subject based on a plurality of location indications of at least one sensor disposed on an intrabody probe within the body cavity, comprises: a non-transitory memory having stored thereon a code for execution by at least one hardware processor, the code comprising: code for receiving data indicative of the plurality of location indications of the at least one sensor disposed on the intrabody probe with the body cavity, code for identifying based on the data at least a first group and a second group of location indications, and code for reconstructing the body cavity from the data, using a first reconstruction method for the first group of location indications, and a second reconstruction method for the second group of location indications.

According to a tenth aspect, a computer implemented method of reconstructing an image of a body cavity shape of a subject based on a plurality of location indications of at least one sensor disposed on an intrabody probe within the body cavity, comprises: receiving the plurality of location indications of the at least one sensor disposed on the intrabody probe with the body cavity, uniformly sampling the plurality of location indications, computing a point density function (PDF) based on the uniformly sampled plurality of location indications, computing a contour function by subtracting a predetermined threshold from the computed PDF, and reconstructing an image of an outer shell of the body cavity according to the contour function.

According to an eleventh aspect, a system for reconstructing a body cavity shape of a subject based on a plurality of location indications of at least one sensor disposed on an intrabody probe within the body cavity, comprises: a non-transitory memory having stored thereon a code for execution by at least one hardware processor, the code comprising: code for receiving the plurality of location indications of the at least one sensor disposed on the intrabody probe with the body cavity, code for uniformly sampling the plurality of location indications, code for computing a point density function (PDF) based on the uniformly sampled plurality of location indications, code for computing a contour function by subtracting a predetermined threshold from the computed PDF, and code for reconstructing an image of an outer shell of the body cavity according to the contour function.

According to a twelfth aspect, a computer program product for reconstructing a body cavity shape of a subject based on a plurality of location indications of at least one sensor disposed on an intrabody probe within the body cavity, comprises: a non-transitory memory having stored thereon a code for execution by at least one hardware processor, the code comprising: instructions for receiving the plurality of location indications of the at least one sensor disposed on the intrabody probe with the body cavity, instructions for uniformly sampling the plurality of location indications, instructions for computing a point density function (PDF) based on the uniformly sampled plurality of location indications, instructions for computing a contour function by subtracting a predetermined threshold from the computed PDF, and instructions for reconstructing an image of an outer shell of the body cavity according to the contour function.

At least some of the systems, methods, apparatus, and/or code instructions described herein improve the technology of reconstructing images of body cavity shapes of a subject based on location indications computed based on data outputted by sensor(s) located on a probe positioned within the body cavity, for example, based on electrical readings obtained by electrodes, magnetic readings obtained by sensor(s), and/or other methods. The improvement may include an increase in accuracy of the reconstructed image of the body cavity in comparison to other reconstructions methods, for example, in terms of an increase in correlation to the actual anatomical body cavity of the subject.

The body cavity may be reconstructed without depicting regions where location indications were not obtained, but which had the potential to contain such location indications by moving the sensor(s) to the respective regions. Such regions absent of location indications would otherwise appear as discontinuous, "tunnels", or "cavities" in the surface of the reconstructed image. At least some of the systems, methods, apparatus, and/or code instructions described herein improve the computing device computing the reconstructed image, and/or improve the computational performance of the computing device computing the reconstructed image, by improving the accuracy of the reconstructed images and/or by removing artifacts from the reconstructed image, for example, surface discontinuities, and/or tunnels through the surface.

At least some of the systems, methods, apparatus, and/or code instructions described herein address the technical problem of differentiating between regions within the received location indications that represent "holes", where location indications are potentially obtained by moving the sensor(s) on the probe to the "holes", and regions within the location indications where location indications cannot be obtained since the sensor(s) on the probe cannot be moved to such regions, for example, regions external to the body cavity. The reconstruction of the image should take the "holes" into consideration and ignore the regions external to the body cavity.

In a further implementation form of the eighth and ninth aspects, the locations indicated by the location indications of the first group are closer to the outer shell of the body cavity than the locations indicated by the location indications of the second group.

In a further implementation form of the eighth and ninth aspects, the identifying of the first and second group of location indications is according to proximity of the indicated locations to an outer shell of the body cavity.

In a further implementation form of the eighth and ninth aspects, each of the first and second reconstruction methods include uniformly sampling the data in the corresponding group.

In a further implementation form of the eighth and ninth aspects, each of the first and second reconstruction methods comprise setting a threshold to point density function describing the density of the location indications in the corresponding group, and the two methods differ in the value of the threshold.

In a further implementation form of the eighth and ninth aspects, each of the point density functions describe the density of a uniform sample of location indications.

In a further implementation form of the eighth and ninth aspects, the first reconstruction method comprises emulating a first non-zero number of location indications, and the second reconstruction method comprises emulating a second number of location indications, the second number being larger than the first number.

In a further implementation form of the eighth and ninth aspects, the first reconstruction method does not emulate location indications, and the second reconstruction method does comprises emulating location indications.

In a further implementation form of the tenth, eleventh, and twelfth aspects, the plurality of location indications comprise a point cloud obtained by maneuvering of the intrabody probe to various spatial locations within a three dimensional (3D) space within the body cavity.

In a further implementation form of the tenth, eleventh, and twelfth aspects, the uniformly sampling of the plurality of location indications assigns an equal weight to each of a plurality of sampling regions associated with varying densities of location indications.

In a further implementation form of the tenth, eleventh, and twelfth aspects, a first sub-set of the plurality of location indications obtained within at least one first region of the body cavity are arranged at a first density, and a second sub-set of the plurality of location indications obtained within at least one second region of the body cavity are arranged at a second density that is lower than the first density, and wherein the uniformly sampling is performed at a same rate for the first and second sub-sets.

In a further implementation form of the tenth, eleventh, and twelfth aspects, the uniform sampling is performed by computing a 3D grid having uniform cell size that includes the location indications, selecting a single location indication for each cell that includes two or more location indications and discarding non-selected location indications.

In a further implementation form of the tenth, eleventh, and twelfth aspects, the PDF is computed by identifying cells of the 3D grid without location indications and cells of the 3D grid with location indications.

In a further implementation form of the tenth, eleventh, and twelfth aspects, the PDF is computed by computing a plurality of distribution functions each centered at the location indication corresponding to a corresponding one of the uniformly sampled plurality of location indications, and computing for each respective point of the 3D grid a sum of the value of all the plurality of distribution functions at that 3D grid point.

In a further implementation form of the tenth, eleventh, and twelfth aspects, the plurality of distribution functions are selected from the group consisting of: Gaussian, and cosine.

In a further implementation form of the tenth, eleventh, and twelfth aspects, the PDF is computed using a nonparametric kernel process.

In a further implementation form of the tenth, eleventh, and twelfth aspects, the outer shell of the body cavity is reconstructed according to the contour function by selecting portions of the contour function that border between positive and negative values.

In a further implementation form of the tenth, eleventh, and twelfth aspects, the value of the predetermined threshold is determined independently of the plurality of location indications.

In a further implementation form of the tenth, eleventh, and twelfth aspects, values of the PDF below the predetermined threshold are determined to be located externally to an inner wall of the body cavity, and values of the PDF above the predetermined threshold are determined to be located within an interior of the body cavity bounded by the inner wall of the body cavity.

In a further implementation form of the tenth, eleventh, and twelfth aspects, the image of the outer shell of the body cavity is based on the values of the contour function denoting location indications within an interior of the body cavity bounded by the inner wall of the body cavity, and values of the contour function denoting location indications external to the inner wall of the body cavity are excluded from the image of the outer shell.

In a further implementation form of the tenth, eleventh, and twelfth aspects, the outer shell is reconstructed from the contour function according to a marching cube computational process.

In a further implementation form of the tenth, eleventh, and twelfth aspects, the method, system, and computer program product further comprise: providing at least one marking indicative of a location of the body cavity where a medical procedure is performed, and reconstructing the image of the outer shell of the body cavity according to the contour function and the at least one marking by computing a mesh denoting the outer shell to intersect each of the at least one marking while maintain an original actual location corresponding to each at least one marking.

In a further implementation form of the tenth, eleventh, and twelfth aspects, markings having the original actual location greater than a predefined outlier distance from the mesh are excluded from the image of the outer shell.

In a further implementation form of the tenth, eleventh, and twelfth aspects, at least one of the plurality of location indications denote the at least one marking.

In a further implementation form of the tenth, eleventh, and twelfth aspects, the method, system, and computer program product further comprise selecting at least one region within the uniformly sampled plurality of location indications, computing a set of emulated location indications within the at least one region, uniformly sampling the set of emulated location indications and uniformly sampling non-emulated plurality of location indications, wherein the PDF is computed based on the uniformly sampled plurality of non-emulated location indications and the uniformly sampled set of emulated location indications.

In a further implementation form of the tenth, eleventh, and twelfth aspects, the at least one region is selected according to a prediction of a plurality of cells of a 3D grid lacking location indications, wherein the 3D grid is used for sampling the plurality of location indications to compute the uniformly sampled plurality of location indications.

In a further implementation form of the tenth, eleventh, and twelfth aspects, the at least one region is located within the interior of the body cavity, away from an inner wall of the body cavity.

In a further implementation form of the tenth, eleventh, and twelfth aspects, selecting the at least one region comprises computing the at least one region according to a predefined distance away from an estimated location indication of an inner wall of the body cavity.

In a further implementation form of the tenth, eleventh, and twelfth aspects, the predefined distance is computed based on a Mahalanobis distance from a computed center of mass of the uniformly sampled plurality of location indications, less than a predefined distance threshold.

In a further implementation form of the tenth, eleventh, and twelfth aspects, computing the set of emulated location indications comprises: computing a second PDF for the selected at least one region, computing a second 3D grid of cells for the selected at least one region, and computing at least one emulated location indication for each cell of the 3D grid, wherein a value of the second PDF corresponding to the respective cell is below a second threshold.

In a further implementation form of the tenth, eleventh, and twelfth aspects, the second threshold is lower than the predefined threshold subtracted from the PDF to compute the contour function.

In a further implementation form of the tenth, eleventh, and twelfth aspects, the body cavity comprises the left atrium, and wherein the selecting the at least one region comprises: identifying a first region with Mahalanobis distances from a center of mass of the uniformly sampled plurality of location indications less than a predefined distance threshold.

In a further implementation form of the tenth, eleventh, and twelfth aspects, the identifying of the at least one region further comprises: identifying a second region according to a set of rules different than the Mahalanobis distances for identifying the first region, unifying the first region and the second region to create the at least one region.

In a further implementation form of the tenth, eleventh, and twelfth aspects, a non-height dimension of the second region is the same as a corresponding non-height dimension of the first region.

In a further implementation form of the tenth, eleventh, and twelfth aspects, a lower border of the second region is according to a predefined height above a bottom of the plurality of location indications within the body cavity.

In a further implementation form of the tenth, eleventh, and twelfth aspects, an upper border of the second region penetrates the first region.

In a further implementation form of the tenth, eleventh, and twelfth aspects, the penetration of the first region by the second region is according to a predefined portion of location indications of the first region.

In a further implementation form of the tenth, eleventh, and twelfth aspects, the predefined portion of location indications of the first region is a predefined percentage of the location indications of the first region.

In a further implementation form of the tenth, eleventh, and twelfth aspects, the predefined distance threshold is about 1.1.

In a further implementation form of the tenth, eleventh, and twelfth aspects, the method, system, and computer program product further comprise presenting the reconstructed image of the outer shell of the body cavity on a display.

In a further implementation form of the tenth, eleventh, and twelfth aspects, the plurality of location indications are computed based on a plurality of electrical readings, magnetic readings, or transformations thereof, made by the at least one sensor disposed on the intrabody probe.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
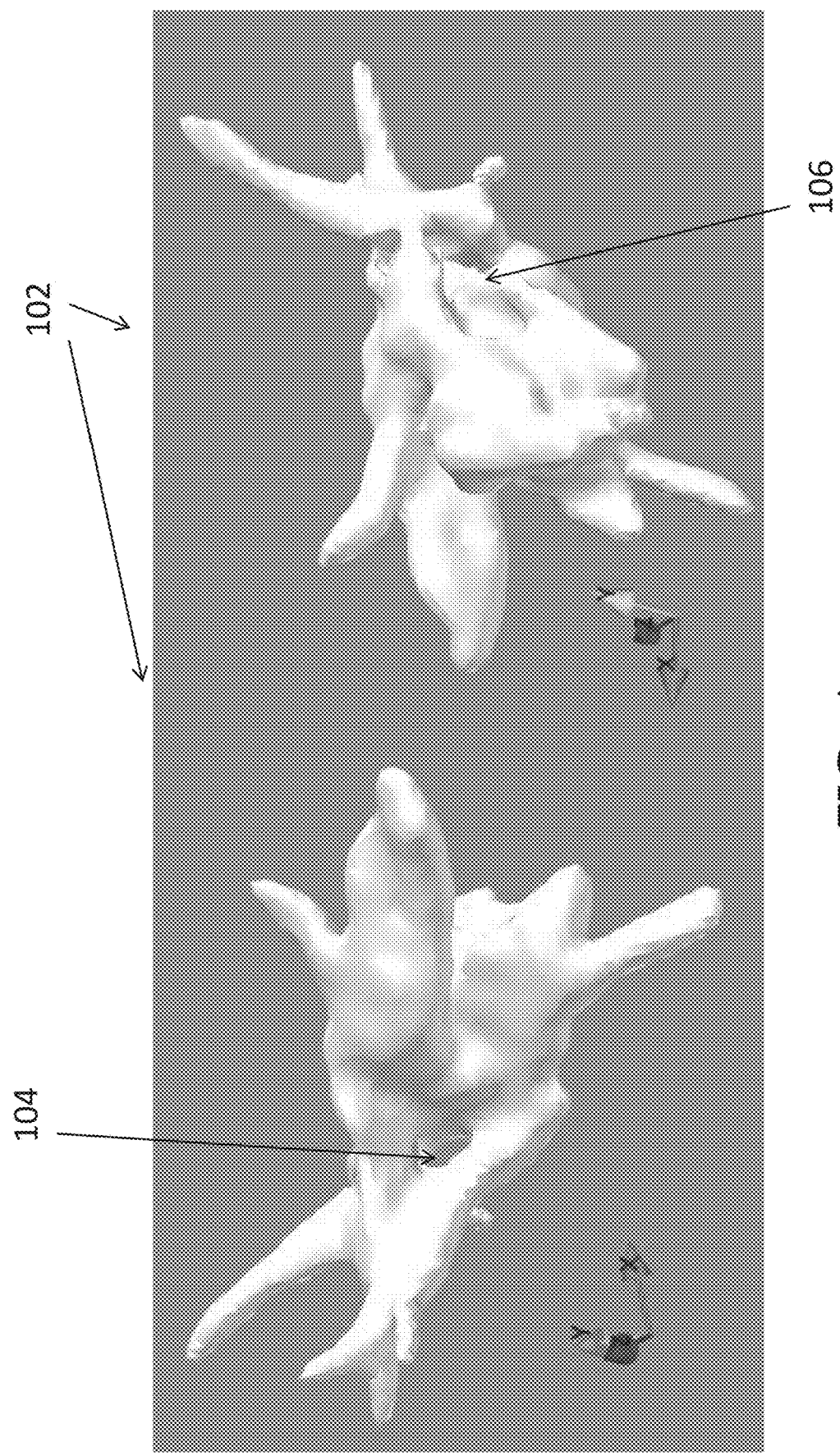
FIG. 1 is a schematic of a reconstructed left atrium image created based on received location indications including "tunnels" through the surface of the reconstructed image, for helping to understand the technical problem addressed by some embodiments of the present invention.

The present invention, in some embodiments thereof, relates to medical imaging and, more specifically, but not exclusively, to systems and methods for reconstruction of a body cavity image.

Along the description, reference is made to some earlier patent applications by the Applicant, detailed in Table 1 below. The contents of the publications recited in Table 1 are incorporated herein by reference in their entirety:

TABLE 1

| Application No. | Publication No. |
| --- | --- |
| PCT IB/2018/050192 | WO 2018/130974 |
| PCT IB/2018055344 | WO 2019/034944 |
| PCT IB/2018/056158 | WO 2019/035023 |
| PCT IB/2018/050784 | WO 2018/146613 |

An aspect of some embodiments of the present invention relates to systems, methods, an apparatus and/or code instruction for generating an image of a body cavity of a subject from location indications. In some embodiments, the image is of a body cavity mapped by a catheter. In some such embodiments, each location indication indicates a location visited by the catheter. The location indications may also be referred to herein in aggregate as a point cloud, in which each location indication is a point in the point cloud. In some embodiments, the image is generated by defining a contour according to a uniform sample of the location indications.

Often, the catheter visits different portions of the body cavity at different intensity. For example, if the catheter is used for providing therapy, the target of the therapy is visited extensively, while other portions of the body cavity are visited mainly when the catheter moves towards or from the target. The intensity may be, for example, density of number of visits per unit area and/or volume, and/or amount of time spent during such visits, such as total amount of time per area and/or volume. As a result, some volumes within the body cavity are not being visited at all, and they may appear as "holes" in the point cloud. In some embodiments, such holes do not appear in the image, as they are dealt with in the process of generating the image from the point cloud. Optionally, a "hole" prone region is identified based on anatomical priors. For example, based on knowledge of the procedure the catheter is used for and the path it is expected to take in the body cavity, it may be possible to predict in advance that certain portions of the cavity (e.g., at the center) will be visited less than other portions (e.g., near a wall defining the body cavity), and thus will be prone to "holes". In some embodiments, the "hole" prone region is filled with emulated location indications. Optionally, the emulated location indications are distributed uniformly. An emulated location indication is a point added to the point cloud, which does not represent a location visited by the catheter (i.e., non-visited location), but rather emulates (i.e., imitates) such a visit.

The emulated location indications may be simulated location indications, i.e. locations visited by the catheter without the physical visit by the catheter actually occurring. For example, the emulated location indications may be stored as simulated points in the point clouds that may have coordinates in the point cloud, without the catheter actually visiting those coordinates. The image of the body cavity is generated from a sample of according to non-emulated location indications (that may indicate a location(s) that have been visited by the probe) and according to a sample of the emulated location indications (that emulate visits that did not occur in fact). In some embodiments, both emulated and non-emulated location indications may be sampled uniformly (e.g., at a same or different sampling rates) and the image is generated based on the uniformly sampled location indications.

An aspect of some embodiments of the present invention relates to systems, methods, an apparatus and/or code instruction for reconstructing a body cavity image of a subject based on location indications computed based on data outputted by sensor(s) located on an intrabody probe (e.g., catheter) positioned within the body cavity, for example, the sensor(s) sense voltage indications which are transformed to the location indications. In some embodiments, the image of the body cavity is generated by defining a contour to a uniform sample of the location indications. The instructions may be stored in a data storage device and executable by one or more hardware processors. The reconstructed body cavity images may be created during an interventional procedure, when the probe, optionally a catheter, is inserted into the body cavity, to perform a medical procedure, for example, an ablation. The body cavity may be, for example, left atrium, other heart chambers, bladder, uterus, aorta, other blood vessels, stomach, other portion of the digestive system, etc. Location indications are obtained at multiple locations throughout the body cavity by maneuvering the probe within the cavity. Optionally, the location indications are uniformly sampled. The uniform sampling reduces and/or prevents bias in the distribution density of the location indications due to bias by the user (e.g., physician performing the procedure) that obtained the location indications. For example, user's bias may lead to a high density of location indications in certain locations and low density of location indications in other regions. High and low density of location indications may appear, for example, due to interest of the physician in the region or lack of such interest.

In an exemplary embodiment, a point density function (PDF) is computed based on uniformly sampled location indications. A contour function is computed by subtracting a predetermined threshold from the computed PDF, and an image of an outer shell of the body cavity is reconstructed according to the contour function. The reconstructed image may be provided for presentation on a display. The reconstructed image may be dynamically created during the procedure, and optionally dynamically updated to increase resolution and/or accuracy of the reconstructed image as additional location indications are obtained while the probe is maneuvered within the cavity during the procedure. Update may also be useful in case the structure changes, e.g., by the medical procedure that takes place, and/or because of physiological changes that the patient goes through (like dehydration, fibrillations, etc.).

Points, i.e., location indications, within a certain region of the point cloud and/or corresponding to different regions in the body cavity, may be referred to herein as groups, e.g., a group of location indications.

Optionally, one or more regions are identified within the point cloud of the location indications as potentially including "holes". Such "holes" are regions inside the body cavity, at which there are very few or no location indications. The information that the regions are inside the body cavity is a prior, and not inferred from the location indications themselves. The regions including "holes" are selected for artificially filling them in, for example, on the basis of being located away from tissue target for treatment and/or located away from the wall of the body cavity, and/or less likely to be visited by the probe for other reason. For example, a blood and/or fluid filled interior of the body cavity may be identified to be less likely visited by the catheter, and thus require "filling in". The selected region is preferably far enough from the inner wall of the body cavity to avoid tampering with the location indications indicative of the actual inner wall. The "holes" are sometimes due to lack of positioning of the sensor(s) of the catheter(s) within the identified regions. For example, if the operator focuses on moving the sensor(s) of the catheter against the inner wall of the cavity rather than within the interior of the body cavity, the density of location indications at the inner wall will increase and away of the inner wall will decrease, so that regions that lack location indications will be created.

In some embodiments, a set of emulated location indications is computed for the identified region(s) (i.e., the region(s) with the "holes"). A selected region including the set of emulated location indications, is uniformly sampled, and the non-emulated location indications are uniformly sampled. A PDF is computed for the uniformly sampled set of emulated location indications and for the uniformly sampled set of non-emulated location indications. Optionally, both sets are uniformly sampled at a same sampling rate, however, in some embodiments, PDFs and/or sampling rates may differ between the regions. The image is reconstructed based on the PDF as described herein.

In some embodiments, a procedure takes place at a treatment site at the wall of the body cavity, and the probe stays at that point for long, thus providing exceptionally detailed data on the location of the treatment site. Thus, in some such embodiments, imaging results of such locations can be exceptionally trust-worthy, and the reconstructed shape of the inner wall is adjusted to go through the treated site, optionally distorted as required for fitting to these trust-worthy points.

Optionally, when one or more markings indicative of a location where a medical procedure (e.g., ablation) is performed are provided, the reconstruction of the outer shell of the body cavity is computed to intersect the markings at their location. The location of the marking is maintained while the outer shell is adjusted during reconstruction to intersect the marking at its maintained location. Optionally, the markings indicative of the medical procedure locations, for example dots, stars, and/or arrows, are presented on the surface of the image of the outer shell.

An aspect of some embodiments of the present invention relates to systems, methods, an apparatus and/or code instruction for reconstructing an image of a body cavity shape of a subject based on location indications computed based on data outputted by sensor(s) disposed on an intra-body probe within the body cavity. In embodiments, a first group and a second group of location indications are identified (e.g., as a group of location indications close to the body cavity wall, and a group of location indications close to the center of the body cavity). The locations indicated by the location indications of the first group are in a different region of the body cavity than the locations indicated by the location indications of the second group. The image of the body cavity is reconstructed using a first reconstruction method for the first group of location indications, and a second reconstruction method for the second group of location indications. For example, the reconstruction methods may differ in one or more of the following: whether or not location indications are emulated at each group, sampling rate at each group, PDF used in each group, a threshold used in each group to obtain a contour function from the PDF, etc. In some embodiments, the reconstruction method is based on dividing the location indications according to, for example, likelihood of corresponding to target tissue likely to be medically treated (e.g., ablation) and likelihood of corresponding to anatomical locations not targeted for medical treatment. Location indications corresponding to target tissue targeted for precise imaging should not be tampered with, while location indications corresponding to tissue that may be imaged in less detail or accuracy may be adapted by including emulated location indications. In another example, the reconstruction method is based on dividing the location indications according to estimation of expected density and/or number of location indications. The emulated location indications are computed for each group according to the estimated amount of "missing" location indications (which may be inferred from the expected estimation and the number of location indications available).

An aspect of some embodiments of the present invention relates to systems, methods, an apparatus and/or code instruction for reconstructing an image of a body cavity shape of a subject based on a point cloud having an inner region where the points are sparser than outside the inner region. Each point of the point cloud represents a location visited by an intra body probe. Points are added to the inner region to emulate additional visits of the intra body probe in the inner region, where the intra body probe has not actually been physically present at the locations corresponding to the emulated points. The points in the point cloud may be uniformly sampled, and the addition of the points being carried out after the uniform sampling. The image of the body cavity shape is reconstructed from the point cloud, after the emulated points are added to the point cloud.

The point cloud with the inner region having sparser points than outside the inner region may represent, for example, locations visited within a body cavity such as a heart chamber, where the inner wall tends to be visited more often than the interior of the chamber, for example, when the physician controlling the intra body probe is navigating the intra body probe against the inner wall for treating the inner wall more often than navigating the probe within the inner region of the chamber which is filled with fluid such as blood.

At least some of the systems, methods, apparatus, and/or code instructions described herein improve the technology of reconstructing images of body cavity shapes of a subject based on location indications computed based on data outputted by sensor(s) located on a probe positioned within the body cavity, for example, based on electrical readings obtained by electrodes, magnetic readings obtained by sensor(s), and/or other methods. The improvement may include an increase in accuracy of the reconstructed image of the body cavity in comparison to other reconstructions methods, for example, in terms of an increase in correlation to the actual anatomical body cavity of the subject. The body cavity may be reconstructed without depicting regions where location indications were not obtained, but which had the potential to contain such location indications by moving the sensor(s) to the respective regions. Such regions absent of location indications would otherwise appear as discontinuous, "tunnels", or "cavities" in the surface of the reconstructed image. At least some of the systems, methods, apparatus, and/or code instructions described herein improve the computing device computing the reconstructed image, and/or improve the computational performance of the computing device computing the reconstructed image, by improving the accuracy of the reconstructed images and/or by removing artifacts from the reconstructed image, for example, surface discontinuities, and/or tunnels through the surface.

At least some of the systems, methods, apparatus, and/or code instructions described herein address the technical problem of differentiating between regions within the received location indications that represent "holes", where location indications are potentially obtained by moving the sensor(s) on the probe to the "holes", and regions within the location indications where location indications cannot be obtained since the sensor(s) on the probe cannot be moved to such regions, for example, regions external to the body cavity. The reconstruction of the image should take the "holes" into consideration and ignore the regions external to the body cavity.

Reference is now made to FIG. 1, which includes two views of a reconstructed left atrium image 102 created based on received location indications. The Image includes "tunnels" 104, 106 through the surface of the reconstructed image. Left atrium image 102 was reconstructed based on location indications generated based on measurements obtained by sensor(s) on a probe maneuvered within a left atrium, without features implemented by at least some of the systems, apparatus, methods, and/or code instructions described herein. Regions in space where location indications have not been obtained create artifacts 104 106 in the reconstructed left atrium image 102, for example, appearing as "tunnels" through the reconstructed surface of the left atrium and/or "cavities" formed due to deformations of the reconstructed surface of the left atrium.

Figure 2:
FIG. 2 is a reconstructed left atrium image created based on received location indications, in accordance with some embodiments of the present invention.

Reference is now made to FIG. 2, which is a reconstructed left atrium image 202 created based on received location indications, in accordance with some embodiments of the present invention. FIG. 2 and FIG. 1 are based on the same data, but FIG. 2 implements embodiments of the present invention. Left atrium image 202 illustrates that embodiments of the present disclosure provide a technical solution to the technical problem described with reference to FIG. 1. Left atrium image 202 has a smooth and/or continuous surface free of artifacts 104 and 106, for example, in comparison to the reconstruction of left atrium 102 shown with reference to FIG. 1, which does include such artifacts.

At least some of the systems, methods, apparatus, and/or code instructions described herein use location indications generated based on measurements obtained by sensors located at multiple locations within a body cavity of a subject, for example, electrical readings obtained by electrodes, to reconstruct an image of an outer shell of the body cavity. In particular, emulated location indications are computed for regions where no location indications are provided to improve the accuracy of the reconstructed image, for example, avoiding artifacts such as discontinuities, and/or tunnels in the outer shell of the body cavity that would otherwise result from lack of non-emulated location indications.

At least some of the systems, methods, apparatus, and/or code instructions described herein are directed to a new and useful technique for using data obtained by sensors, such as electrodes located on the distal end portion of a probe (e.g., catheter) located within the body cavity, to more efficiency reconstruct an image of an outer shell of the body cavity, in particular, to increase the accuracy of the reconstructed image of the outer shell of the body cavity and/or avoid artifacts in the reconstructed image.

At least some of the systems, methods, apparatus, and/or code instructions described herein address the technical problem of reconstructing an image of an outer shell of a body cavity of a subject from location indications, when the distribution of the location indications is non-uniform, and may vary drastically between neighboring locations. For example, many location indications are obtained close together within one region (i.e., high density), and few location indications are obtained far apart within another region (i.e., low density), which may be located in proximity to the first region or further away from the first region. At least some of the systems, methods, apparatus, and/or code instructions described herein accurately reconstruct such regions by addressing the technical problem differently at different regions, for example, to create a smooth and/or high resolution and/or accurate representation and/or reduced-artifacts of the anatomical structure of the body cavity.

At least some of the systems, methods, apparatus, and/or code instructions described herein address the technical problem of reconstructing an image of an outer shell of a body cavity of a subject from point clouds, e.g., of location indications when the set of obtained location indications include regions expected to include holes (i.e., regions in which there are no, or very low density location indications). In some embodiments, the location indications are generated from measurements obtained by sensors of a catheter positioned at multiple locations within the body cavity. In such embodiments, location indications may be obtained from locations where the sensors are located while contacting the inner tissue of the body cavity and/or floating within blood and/or other fluids within the interior of the body cavity away from the inner wall. The technical problem relates to how to handle such "holes" in the reconstruction of the image of the outer shell of the body cavity of the subject. In some implementations, the technical solution to the technical problem is based on computing a set of emulated location indications within the "holes", and reconstructing the image of the outer shell of the body cavity based on the non-emulated location indications and the emulated location indications.

At least some of the systems, methods, apparatus, and/or code instructions described improve the technology of reconstructing images of body tissues for ablation, by using location indications that are more or less trust-worthy in a manner that makes use of knowledge of their trust-worth. The degree of trust-worthiness may be based on whether the respective location indications denote ablated tissue (i.e., more trust-worthy, because the catheter remained there for a significantly long time interval during the ablation) or tissue not ablated (i.e., less trust-worthy). In embodiments, the more trust-worthy locations are marked, for example, as markings of ablated tissue. The technology is improved by enforcing the reconstruction process to go through the locations indicated by the more trust-worthy location indications, and/or allow more flexible reconstruction of the less trust-worthy location indications. The reconstructed image is more accurate in regions that correspond to ablated tissues and may be less accurate for the regions that correspond to tissues that are not ablated. In embodiments where the outer shell of the reconstructed image does not go through each location indicated by the location indications, each location indication, including indications corresponding to locations at which a medical procedure, for example ablation, was performed may appear to "float" above or below the surface of the outer shell of the body cavity. In some implementations, the technical improvement is based on computing the reconstructed shell to intersect each marking, to create an image where the location of the marking is on the surface of the reconstructed shell. In some embodiments, if the marking is far from the reconstructed shell surface by more than a predetermined threshold, the shell is not corrected to intersect it, and the marking floats. Such embodiments may be implemented, for example, where going through the markings might distort too heavily the entire reconstruction.

Figure 8:
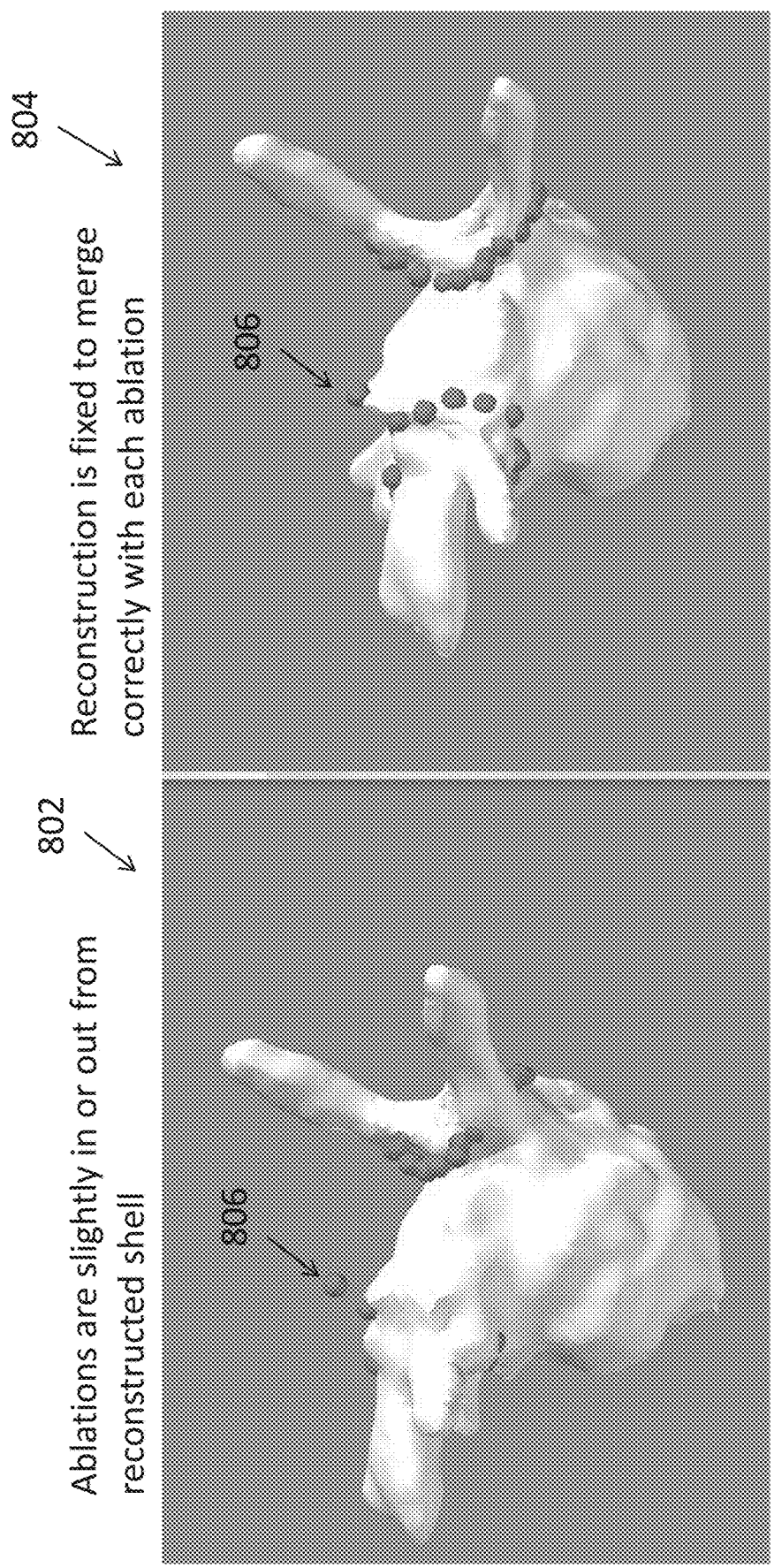
FIG. 8 is a schematic depicting a reconstruction of a left atrium including procedure markings denoting location of ablations in a left atrium created using other methods, and a schematic depicting a reconstruction of the left atrium including procedure markings denoting location of ablations in a left atrium created in accordance with some embodiments of the present invention.

Reference is now made to FIG. 8, which is a schematic 802 depicting a reconstruction of a left atrium including procedure markings denoting location of ablations in a left atrium before correction, and a schematic 804 depicting a reconstruction of the left atrium including procedure markings denoting location of ablations in a left atrium after correction, created in accordance with some embodiments of the present invention. It is noted that in schematic 802, the left atrium may be reconstructed as described herein. Ablation markings appear slightly above or below the reconstructed shell of the left atrium, for example, ablation marking 806 is shown elevated above the surface of the left atrium. Ablation marking 806 represents a trust-worthy location indication, due to the catheter spending a significant amount of time at the corresponding physical location to perform the ablation procedure. In comparison, since ablation marking 806 represents a trust-worthy location, in schematic 804 the shell of the left atrium is reconstructed to intersect the trust-worthy ablation markings, which is known to be physically located at the surface of the left atrium, so that ablation marking 806 appears on the surface of the left atrium, rather than free floating above the surface.

At least some of the systems, methods, apparatus, and/or code instructions described herein improve an underlying technical process within the technical field of medical imaging, in particular, within the technical field of reconstructing an image of an outer shell of a body cavity of a subject from location indications, for example, from location indications generated based on measurements obtained by electrodes positioned at multiple locations within the body cavity.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 3A:
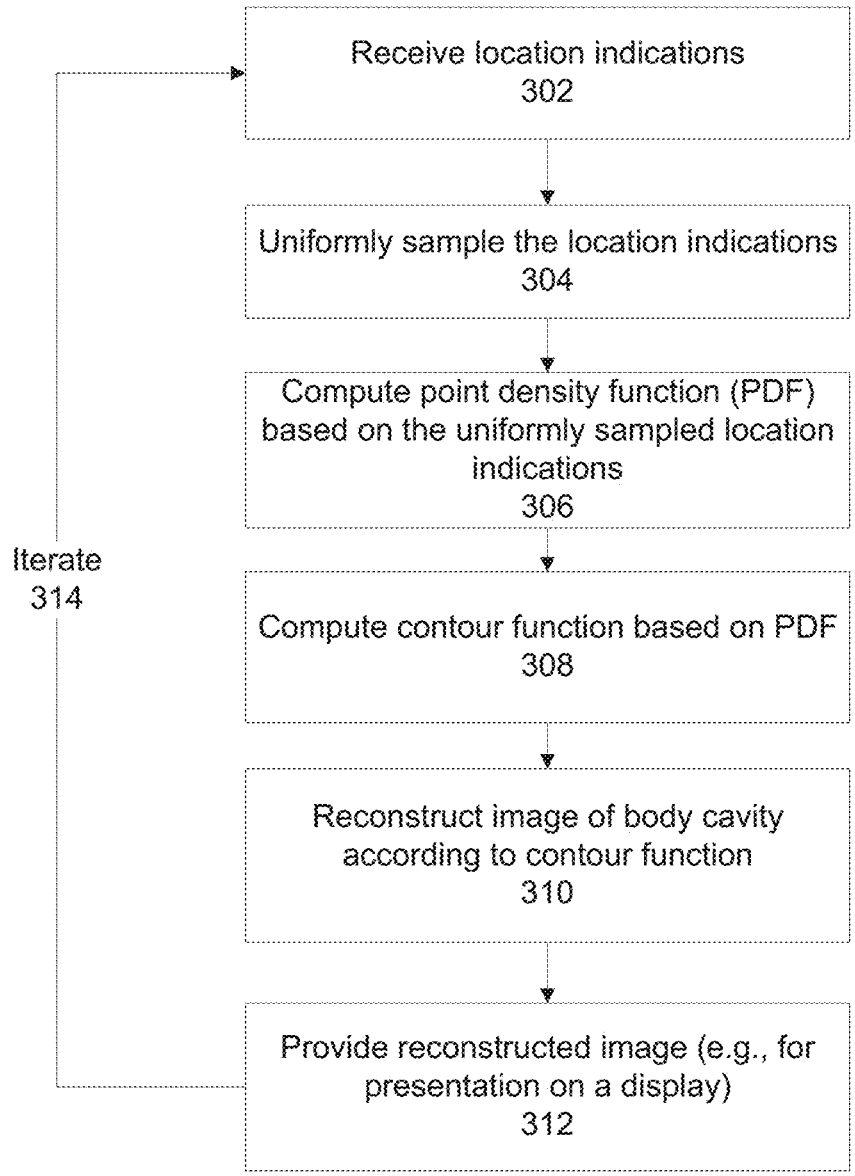
FIG. 3A is a flowchart of a method of reconstructing a body cavity image of a subject based on location indications computed based on data outputted by sensor(s) on an intrabody probe within the body cavity, in accordance with some embodiments of the present invention.
Figure 3B:
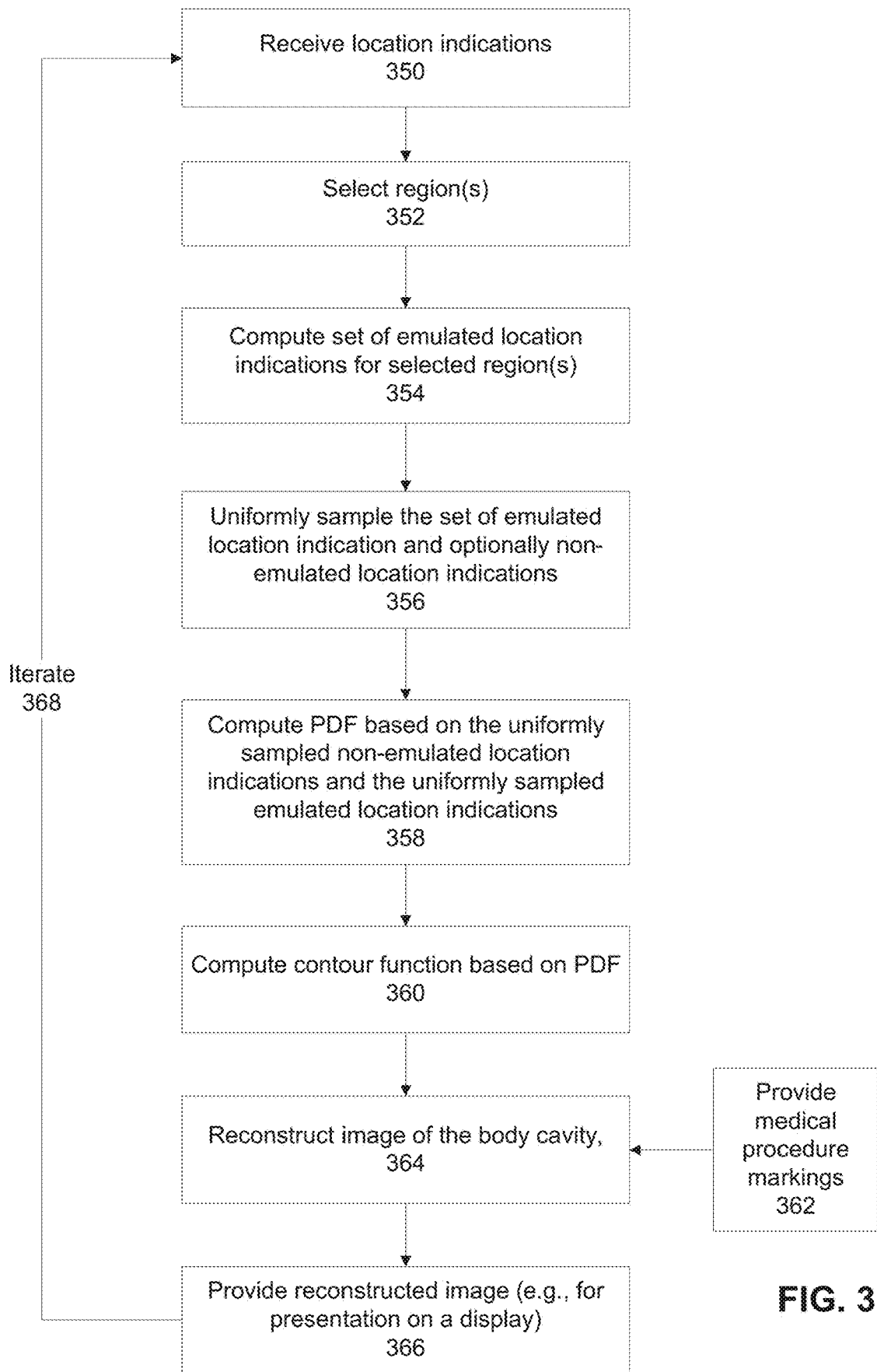
FIG. 3B is a flowchart of a method of reconstructing a body cavity image based on a set of emulated location indications for selected region(s) of the location indications, in accordance with some embodiments of the present invention
Figure 4:
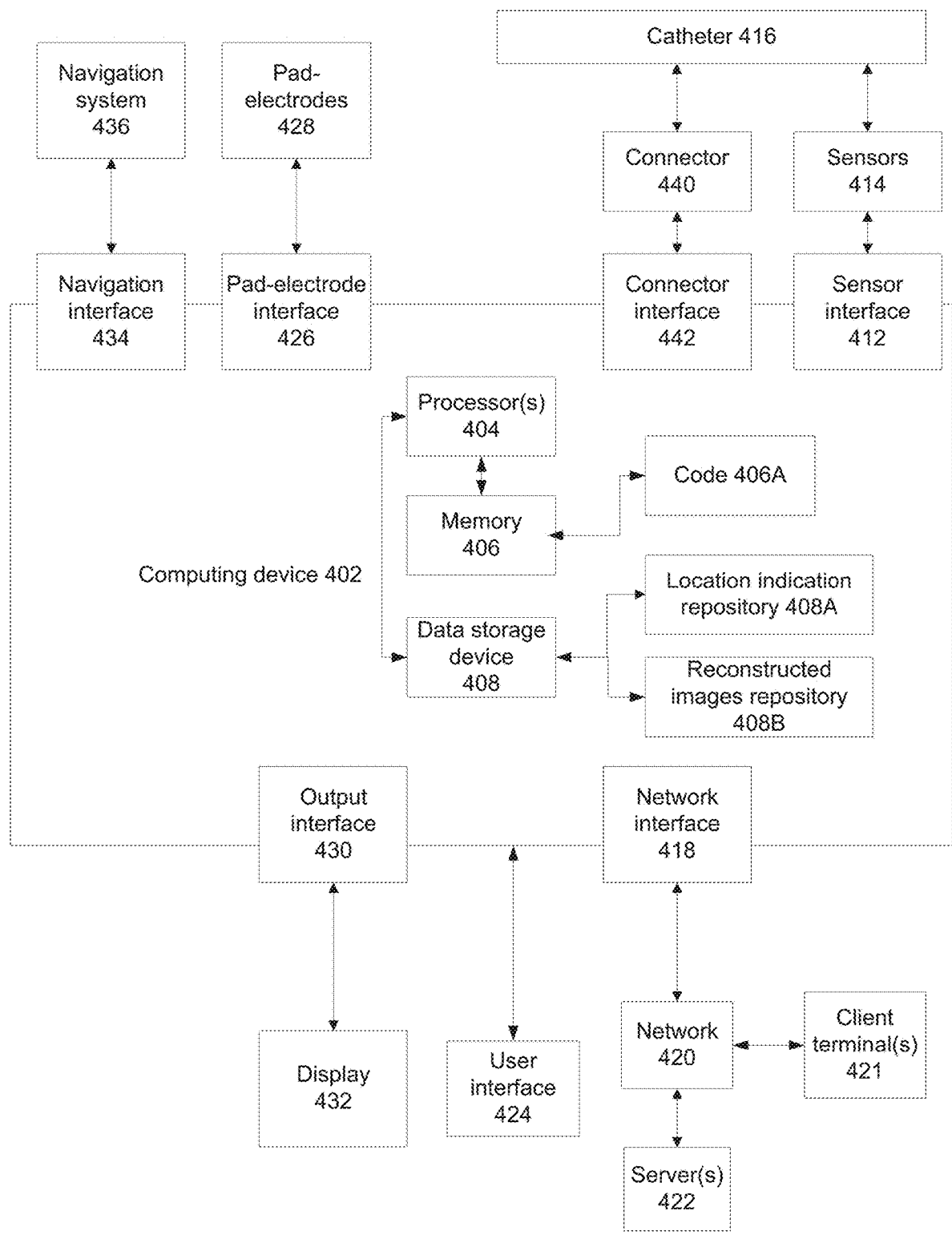
FIG. 4 is a block diagram of components of a system for reconstructing a body cavity image of a subject based on location indications computed based on data outputted within the body cavity, in accordance with some embodiments of the present invention.

Reference is now made to FIG. 3A, which is a flowchart of a method of reconstructing a body cavity image of a subject based on location indications computed, for example, based on data outputted by sensor(s) on an intrabody probe within the body cavity, in accordance with some embodiments of the present invention. Reference is also made to FIG. 3B, which is a flowchart of a method of reconstructing a body cavity image based on a set of emulated location indications for selected region(s) of the location indications, in accordance with some embodiments of the present invention. The region(s) are selected based on an expectation of including "holes" lacking location indications, but having the potential to include such location indications, for example, within the body cavity where the sensor(s) on the catheter were not positioned by the operator but having the potential to be positioned there by the operator. Reference is also made to FIG. 4, which is a block diagram of components of a system 400 for reconstructing a body cavity image of a subject based on location indications computed based on data outputted within the body cavity, in accordance with some embodiments of the present invention. System 400 may implement the acts of the method described with reference to FIGS. 3A-3B, optionally by a hardware processor(s) 404 of a computing device 402 executing code instructions 406A stored in a memory 406.

Computing device 402 may be implemented as, for example, a client terminal, a server, a computing cloud, a virtual server, a virtual machine, a radiology workstation, a workstation installed within a catheterization laboratory, a mobile device, a desktop computer, a thin client, a Smartphone, a Tablet computer, a laptop computer, a wearable computer, glasses computer, and a watch computer.

Multiple architectures of system 400 based on computing device 402 may be implemented. For example, computing device 402 may be implemented as an existing device (e.g., client terminal) having software (e.g., code 406A) that performs one or more of the acts described with reference to FIGS. 3A-3B, for example, code 406A is installed on a computer conventionally existing in a catheterization/interventional lab. In another implementation, computing device 402 may be implemented as a dedicated device, having software (e.g., code 406A) installed thereon.

In another exemplary implementation, computing device 402 storing code 406A may be implemented as one or more servers, for example, network server, web server, a computing cloud, a virtual server, a radiology server, an interventional laboratory server, that provides services based on one or more of the acts described with reference to FIGS. 3A-3B to one or more client terminals 421 over network 420. Client terminal 421 may be, in some embodiments, a terminal located remotely from computing device 402, for example, an interventional/catheterization laboratory client having access to computing device 402 acting as a server. In such as implementation, for example, remotely obtained location indications are transmitted from respective client terminals 421 to computing device 402 over network 420 for reconstruction of the image of the body cavity. The reconstructed image is transmitted from computing device 402 over network 420 to the respective client terminal 421 for presentation on a display associated with the respective client terminal 421.

Hardware processor(s) 404 may be implemented for executing code 406A for implementing the acts of the method described with reference to FIGS. 3A-3B. In some embodiments, hardware processor(s) 404 may be implemented as a central processing unit(s) (CPU), a graphics processing unit(s) (GPU), field programmable gate array(s) (FPGA), digital signal processor(s) (DSP), and/or application specific integrated circuit(s) (ASIC). Processor(s) 404 may include one or more processors, which may be homogenous or heterogeneous, which may be arranged for parallel processing, as clusters and/or as one or more multi core processors.

Memory 406 stores code instructions executable by processor(s) 404. Memory 406 may be for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 406 stores code 406A.

Computing device 402 may include a sensor interface 412 for communicating with one or more sensors 414 located on a distal end portion of catheter 416, for example, sensors 414 may include electrodes. The location indications are computed according to data outputted by sensors 414. Sensors 414 may be designed for intra-body navigation and/or for performing a medical procedure, for example, an electrophysiology (EP) ablation catheter, and/or other ablation catheter designed for chemical ablation, and/or injection catheter, or any other kind of catheter and/or tool.

In one example, the electrodes perform an ablation procedure, perform the reading for outputting data indicative of the location indication, and provide the marking indicative of the location of the ablation procedure. The reconstruction of the body cavity may be performed according to the location indication(s), including the markings indicative of locations of ablation, as described herein.

In some embodiments, data indicative of the location indication of the sensor(s) 414 may be dynamically obtained and/or computed, for example, based on an analysis of electrical readings made by sensor(s) 414 of catheter 416 sensing electric fields generated by pad-electrodes 428. Pad-electrodes 428 may be controlled via a pad-electrode interface 426. Pad-electrodes 428 are positioned externally to the body of the patient for example, on the skin of the patient, and/or in the bed supporting the patient during the intervention, and generate electrical fields. Electrical signals based on the electrical fields are used to estimate the position of catheter 416 within the body cavity. The voltage the pad-electrodes 428 generate is measured by sensors (e.g., electrodes) 414 on catheter 416 and processed to determine the location indications, indicative to the location of the sensors and/or of the electrode at the time of measurement by the sensors of the voltage generated by the pad-electrodes.

In some embodiments, a combination of magnetic and electrical fields is sensed by magnetic sensors and/or electrodes implementations of sensor(s) 414 of catheter 416.

In some embodiments, the location indications are computed based on an analysis of signals obtained by a catheter navigation system 436, optionally a non-fluoroscopic navigation system. The navigation system may be based, for example, or obtaining and processing magnetic sensors and/or electrical sensors. Optionally, the navigation system is an electrical impedance measurement based system. Catheter navigation system 436 may be in communication with computing device 402 via a navigation interface 434, for example, one or more of: a wire connection, a wireless connection, a software interface (e.g., SDK, API), a virtual interface, a network interface, and a local bus. Catheter navigation system 436 may be implemented, for example, as code locally stored on computing device 402, a mechanism designed to move the catheter inside the body automatically based on the code, semi-automatically and/or manually, and/or code running on an external server.

Computing device 402 may include an output interface 430 for communicating with a display 432, for example, a screen or a touch screen. Optionally, the reconstructed image of the outer shell of the body cavity is presented on display 432. Indications of ablated regions may be presented on the outer shell of the body cavity, for example, as dots, starts, and/or other markings, as described herein.

Optionally, computing device 402 includes a network interface 418, for communicating with server(s) 422 over a network 420, for example, to obtain code 406A such as an updated version thereof, and/or transmit the reconstructed image of the body cavity shape of the subject to server(s) 422. Network interface 418 may be implemented as, for example, one or more of, a network interface card, a wireless interface to connect to a wireless network, a physical interface for connecting to a cable for network connectivity, a virtual interface implemented in software, network communication software providing higher layers of network connectivity, and/or other implementations.

Network 420 may be implemented as, for example, the internet, a local area network, a virtual network, a wireless network, a cellular network, a local bus, a point to point link (e.g., wired), and/or combinations of the aforementioned.

Optionally, a user interface 424 is in communication with computing device 402. User interface 424 may include a mechanism for the user to enter data, for example, a touch screen, a mouse, a keyboard, and/or a microphone with voice recognition software. In some embodiments, the user may enter data via a graphical user interface (GUI) presented on display 432, where the GUI acts as user interface 424. Optionally, computing device 402 includes a connector interface 442 that communicates with a connector 440 connecting to catheter 416, for example, RF ablation catheter, injection catheter, navigation catheter, imaging catheter, and/or mapping catheter. Connector 440 may be used, for example, to transmit control signals to catheter 416 to control administration of an intervention medical procedure, for example, control the RF ablation electrodes for an ablation procedure.

It is noted that one or more interfaces 418, 412, 426, 430, 434, 442 may be implemented, for example, as a physical interface for example, cable interface, wireless interface, network interface, and/or as a virtual interface for example API, SDK. The interfaces may each be implemented separately, or multiple (e.g., a group or all) interfaces may be implemented as a single interface.

Processor 404 may be coupled to one or more of memory 406, data storage device 408, and interfaces 418, 412, 426, 430, 434, 442.

Optionally, computing device 402 includes data storage device 408, for example, for storing: location indication repository 408A that stores location indications computed based on data outputted from within the body cavity of the subject, and/or a reconstructed images repository 408B that stores the reconstructed image of the outer shell of the body cavity based on the location indications. Data storage device 408 may be implemented as, for example, a memory, a local hard-drive, a removable storage device, an optical disk, a storage device, and/or as a remote server and/or computing cloud (e.g., accessed using a network connection).

It is noted that computing device 402 may include one or more of the following components: processor(s) 404, memory 406, data storage device 408, and interfaces 418, 412, 426, 420, 434, 442, for example, as a stand-alone computer, as a hardware card (or chip) implemented within a current computer, for example, catheterization laboratory computer, and/or as a computer program product loaded within the current computer.

At 302, location indications, indicative of locations of sensor(s) 414 located on the intrabody probe (e.g., catheter) 416 within the body cavity are received.

Receiving the location indications may include computing locations of the sensors, for example, based on electrical readings and/or magnetic readings, made by the sensor(s) located on the intrabody probe and received by processor 404, for example, from memory 406. The computing may include applying a transformation to such readings. Accordingly, in some embodiments, the location indications are computed based on electrical and/or magnetic readings made by the sensor(s) located on the intra-body probe or transformations of such readings.

It is noted that while the location indications indicate a location of a sensor, the indicated locations are not necessarily the precise location of the sensor, and embodiments of the present invention may differ in the accuracy of these indications.

Optionally, location indications with unacceptably poor accuracy are excluded and/or removed from the location indications, for example, by an automated process that removes outliers and/or by an automated process that identifies inaccurate location indications.

The location indications may be referred to as a point cloud. For example, each location indication may be considered a point in a cloud.

Location indications may be obtained by respective sensors 414 located on the distal end portion of catheter 416, located within a body cavity, for example, a chamber of an organ and/or a lumen (e.g., blood vessel), for example, within the heart, within the bladder, within the digestive system, within the aorta, and/or within the uterus.

The transformation of the electrical and/or magnetic readings is to a location indication within a space at which the electrode that obtained the electrical reading is located. In some embodiments, electrical readings may be transformed into location indications as described in Applicants' patent applications WO 2018/130974, WO 2019/034944, WO 2019/035023, and/or WO 2018/146613.

The location indications may be obtained from storage on a data storage device, for example, from location indication repository 208A of data storage device 208. Alternatively or additionally, the location indications are obtained dynamically, such as in real time from the sensor(s).

Location indications may be obtained by sensor(s) 214 located on a distal end portion of catheter 216, located within the body cavity of the subject.

The location indications may be obtained during an initial phase of the procedure, for example, before treatment procedure, such as ablation, has begun. For example, as an imaging phase to reconstruct the image of the outer shell of the body cavity prior to the actual ablation. The treating physician navigates catheter 216 within the body cavity, collecting location indications from different regions of the body cavity via electrodes 214 on the distal portion of catheter 216.

Optionally, multiple location indications are received, each from a different sensor 214 mounted on catheter 216. Optionally the location indications may include indications generated based on measurements performed by different sensors simultaneously, for example, within a tolerance requirement, which may represent an insignificant amount of time. For example, an amount of time during which the catheter does not move significantly, so measurements performed simultaneously by different sensors on a same probe may be all attributed to the same location of the probe.

The different sensors 414 mounted on the catheter 216 are optionally mounted along a longitudinal axis of the catheter at a distal, rigid, end region of the catheter. Some of the sensors or all of them are optionally mounted along a rigid portion of the distal end region of the catheter.

For example, using an EP (electrophysiology) catheter 216 having a single tip electrode and 3 ring electrodes, the tip electrode may be used as the sensor, in addition to one or more of the ring electrodes.

The location indications may be generated by one or more of the following exemplary implementations: patch electrodes 228 located externally to the target individual that apply multiple alternating currents each at a respective frequency; additional sensor(s) on an additional intra-body catheter (i.e., additional to catheter 216) located in proximity to electrodes 214 that obtain the location indications, and/or additional sensor(s) on an additional intra-body catheter located in a predefined anatomical region, for example, within the coronary sinus as described with reference to U.S. Provisional Patent Application No. 62/449,055 "CORONARY SINUS-BASED ELECTROMAGNETIC MAPPING" by the same assignee and common inventors. In yet another implementation, the location indications may be generated by the same probe. The same probe generates an electrical field and measures the electrical field to obtain the location of the electrodes that obtain the location indications. Such probe is described, for example, with reference to International Patent Application No. IB2018/050784 "INTRABODY PROBE NAVIGATION BY ELECTRICAL SELF-SENSING" by the same assignee.

Exemplary location indications may be based on electrical and/or magnetic readings, including measurements of one or more of the following: voltage, impedance, endocardial electrical activity, electrical activity, dielectric property, S-parameters, and combinations of the aforementioned. It is noted that under the assumption of a constant current, differences in voltage may be translated to differences in impedance. Impedance is not necessarily measured directly and absolutely.

The location indications may include impedance electrical readings indicative of impedance of tissue touching the electrodes when the impedance electrical readings are read.

The location indications may be generated according to voltage readings relative to patches (e.g., pad-electrodes 428) positioned outside the body of the patient, where the patches provide a coordinate system that is fixed in relation to the body of the patient. Optionally a set of 3 pairs of patches are used, through which a low current in three distinct frequencies is applied. The 3 pairs of patches are positioned to correspond to three axes, X, Y, and Z. In some embodiments, the three axes are orthogonal to each other, but in some embodiments orthogonality is compromised, in favor of, e.g., comfortable attachment of the patches to the patient's skin. The measured potentials difference, Vx, between one patch (e.g., pad-electrode 428) and electrode 414 inside the patient's body indicates the position of the electrode 414 along the "X" axis. Optionally, Vx, Vy, and Vz are each monotonic functions along their respective axis. It is noted that impedance may be used to indicate proximity to the inner blood vessel wall, and/or proximity to the pulmonary veins.

Systems and methods of body cavity reconstruction and/or navigation are described in Applicants' patent applications, WO 2018/130974, WO 2019/034944, WO 2019/035023, and Building, for example, on descriptions in those applications, the current inventors have found that the combined use of locally calibrating spatial constraints and/or coherence constraints can be used in some embodiments of the present invention to compute the location indications. In some embodiments, maps of how the location indications are expected to distribute in space, at least approximately, are used as constraints. For the case of voltage-guided navigation techniques, this can be based, for example, on simulations of electrical field voltages in space, wherein the simulations may incorporate descriptions of electrode configurations and/or body tissue dielectric properties.

It is noted that electrical fields may vary as a result of phasic motions such as heartbeat and/or respiration. Patent application WO 2018/130974 describes optional methods of introducing corrections for such phasic motions which are optionally used in conjunction with some embodiments of the present invention.

The location indications may include and/or denote positions of electrical readings indicative of anatomical positions of the sensor(s) when the location indications are read. Each anatomical position is associated with an anatomical structure, for example a specific vein, a specific artery, or a specific anatomical feature of tissue. For example, the location indications may be analyzed to identify a signature pattern association with a certain anatomical structure, for example, a certain heart valve, coronary sinus, or other anatomical structure. Each location indications may be computed according to a reference to a coordinate system. The coordinate system may be fixed relative to the body of the patient, for example, a three dimensional space within which the organ is located. The external coordinate system may be defined by voltage readings obtained by the electrodes relative to the pad electrodes 228 located on the body of the patient, as described herein. In some embodiments, the coordination system is not external, but rather defined in respect to tissue structures or landmarks. For details, see, for example, WO 2019/034944.

At 304, the location indications are uniformly sampled. The uniform sampling of the location indications is performed to address the technical problem arising from non-uniform densities of location indications that may arise from the way the body part is visited by the probe more than by the structure of the body part, as described herein in additional detail. The uniformly sampled location indications are used to create an improved reconstruction of the body cavity, for example, without tunnels, cavities and/or discontinuities, as described herein in additional detail.

The uniform sampling of the location indications assigns an equal weight to each sampling region associated with varying densities of location indications. For example, a rectangular grid of cells, optionally 3D, may be used to define sampling regions. The cells within the grid may be of uniform size, for example smaller cells may provide a higher resolution and/or accuracy to the PDF in comparison with larger cells. The grid of cells may be a virtual grid that virtually divides the point cloud made of the location indications indicating where the catheter has visited. The cell size may be selected according to desired accuracy and/or resolution of the reconstructed image. Within each grid cell, there may be a different number of location indications. In some embodiments, the uniform sampling replaces all the location indications in each grid cell with a single, representative, indication. For example, when the grid cells are of a size 2 millimeters (mm)×2 mm, cells that have one or more location indications are assigned an indication, and cells that are empty may be left empty. It is noted that the grid cell is an exemplary process for dividing a space, and other processes for dividing the space may be used. In some embodiments, empty grid cells remain empty after the uniform sampling. The uniform sampling creates a uniform density of the location indications. For example, location indications obtained within one region of the body cavity may be arranged at a first density, while other location indications obtained within another region of the body cavity are arranged at a different density, for example, lower or higher than the first density. In some embodiments, the uniform sampling of the location indications of both regions is performed at the same sampling rate for each (i.e., both) of the regions.

Optionally, the uniform sampling is performed by computing a 3D grid having a uniform cell size. The entire set of location indications is located within the 3D grid, such that each location indication is mapped to a certain cell of the 3D grid. A single location indication is selected for each cell that includes two or more location indications. The non-selected location indications are discarded. The single location may be selected, for example, as the location indication that has a distance (e.g., Euclidean distance) closest to a predefined location (e.g., center) of the cell. Alternatively, a single location indication is set at a predefined location (e.g., center) of the cells as a replacement for all location indications within the cell.

The size of each cell may be selected according to the desired resolution of the reconstructed image, and/or according to the resolution of the sensor that senses the location indications. For example, smaller cells may result in higher resolution of the reconstructed image, but cells that are too small may introduce noise into the data, for example, by inaccurately representing the actual anatomical location of the location indications. The size of the grid cells may be determined, for example, based on input entered via user interface 424.

At 306, a point density function (PDF) is computed based on the uniformly sampled location indications. The PDF is indicative of density of the location indications at points in space, optionally the PDF is a continuous function, defined for every point in space, contrary to the location indications that are limited to specific points in space, for example, to the center of each grid cell.

Optionally, computing the PDF includes identifying cells of the 3D grid without location indications and cells of the 3D grid with location indications.

Optionally, computing the PDF is based on the cells of the 3D grid with location indications, and ignores cells of the 3D grid without location indications.

Optionally, the PDF is computed by computing multiple distribution functions, where each respective distribution functions is centered at one of the location indications of the uniformly sampled location indications. For example, when each location indication is located at the center of the respective cell of the 3D grid, each distribution function is centered with its respective cell. A sum of the value of all the distribution functions is computed for each respective point in the 3D grid. This way, points belonging to gird cells that had no location indication may still have a positive PDF value.

The distribution function may be selected, for example, according to a function that models the actual location of the location indication based on an error in sensing the actual location. Exemplary distribution functions include: Gaussian, cosine, and other functions that decrease in value from the center.

Optionally, the PDF is computed using a nonparametric kernel process.

At 308, a contour function is computed by subtracting a predetermined threshold from the computed PDF. In some embodiments, the predetermined threshold may be determined based on input from user interface 424. In some embodiments, the threshold is predetermined in the sense that it is determined before obtaining the readings and/or before computing the PDF.

Optionally, the value of the predetermined threshold is determined independently of the location indications. The value of the predetermined threshold may be determined, for example, based on trial and error of multiple cases, by selecting multiple different values and evaluating the resulting reconstructions obtained by each of the multiple different values. Reconstructions may be evaluated to determine whether target detailed structures (e.g., target blood vessels) are accurately depicted (e.g., may be distinguishable from one another), or whether structures are merged by the reconstruction. In some embodiment, the value that results in the best reconstruction in which the target detailed structures are most delineated and visible is selected. The value selection process may be performed off-line for different types of target detailed structures, prior to execution of the reconstruction method, and saved in a dataset according to target structure type. The value may be selected in real-time according to the target detailed structure involved in the current procedure being performed. The value selection process may be performed manually by an operator trying different values and visually evaluating the reconstruction, and/or by code that tries different values and automatically evaluates the reconstruction.

Optionally, the threshold is selected to define between a first group of locations located externally to an inner wall of the body cavity, and a second group of locations associated located within an interior of the body cavity bounded by the inner wall of the body cavity.

Optionally, locations where the values of the PDF is on one side of the predetermined threshold (e.g., below the threshold) are determined to be located externally to an inner wall of the body cavity, and locations where the values of the PDF is on the other side of the predetermined threshold (e.g., above the threshold), are determined to be located within an interior of the body cavity bounded by the inner wall of the body cavity. The threshold may be selected, for example, based on a desired margin of safety, according to the expected errors in the location indications, and/or according to the size of the cavity. The threshold may be selected from a set of predefined thresholds stored in a dataset in a memory, for example, according to the type of body cavity and/or according to the type of procedure being performed. The selection may be performed automatically by code and/or manually by the user.

At 310, an image of an outer shell of the body cavity is reconstructed according to the contour function. The outer shell is reconstructed from the contour function according to a reconstruction process, for example, a marching cube computational process. In some embodiments, the value of the contour function at each point is the value of the PDF at that point, minus the predetermined threshold.

The image of the outer shell of the body cavity is reconstructed from the values of the contour function denoting location indications within an interior of the body cavity bounded by the inner wall of the body cavity. Locations associated with values of the contour function that indicates locations external to the inner wall of the body cavity are excluded from the image of the outer shell.

Optionally, the outer shell of the body cavity is reconstructed according to the contour function by selecting portions of the contour function that border between positive and negative values. The selected portion of the contour function may be equal to zero, or have a value that is effectively zero, for example, within a tolerance range.

At 312, the reconstructed image of the outer shell of the body cavity is provided. The reconstructed image may be presented on a display, for example, in real time during the medical procedure. The reconstructed image may be viewed by the physician during the medical procedure, for navigation of a catheter within the reconstructed image, for example, for positioning the catheter within the body cavity for ablation of tissues of the wall of the body cavity. Alternatively or additionally, the reconstructed image is transmitted to a remote client terminal. Alternatively or additionally, the reconstructed image is stored, for example, in the reconstructed image repository, within a PACS server, and/or within the electronic medical record of the subject.

Referring now back to FIG. 3A, at 314, acts 302-312 are iterated for updating the reconstructed image of the outer shell of the body cavity. The updating may be dynamically performed in real time during the medical procedure. The additional location indications may be dynamically obtained as part of the medical procedure, as the physician navigates the catheter for performing the medical procedure, and not necessarily for collecting additional location indications. Alternatively or additionally, the additional location indications are obtained by the physician for improving the resolution of the reconstructed image, by maneuvering the catheter within the body cavity to collected additional location indications.

Referring now back to FIG. 3B, at 350, location indications are received as described with reference to act 302 of FIG. 3A.

At 352, one or more regions within the location indications are selected. The regions(s) are selected according to an expectation of including "holes", where no location indications are present. Such "holes" are created, for example, when the sensor has not been positioned at certain anatomical locations, and/or where data obtained by the sensor(s) is discarded for example, inaccurate, erroneous, and/or incorrectly labeled as an outlier. "Holes" may be inadvertently created, for example, when the physician maneuvers the catheter to certain anatomical locations of the body cavity as part of the medical procedure, and ignores other anatomical locations which are not relevant to performing the medical procedure. The ignored anatomical locations lack location indications, and this way "holes" may be created.

Location indications, obtained by the catheter actually physically visiting the physical location and/or including emulated location indications, may be arranged into groups corresponding to the different regions.

It is noted that the selection of the regions may be performed whether the regions actually includes "holes", or whether the regions doesn't include holes. The region that doesn't include "holes" may include a sufficient distribution of location indications where no "holes" are present. When regions are selected but no "holes" are present the increased computational cost incurred in processing the regions, in comparison to executing FIG. 3A without selection of region is insignificant, resulting in a non-significant amount of extra processing time.

It is noted that the "holes" may include a low density distribution of location indications, or may be entirely void of location indications.

The regions may be selected within the uniformly sampled location indications. The uniform sampling of the location indications is performed as described with reference to act 304 of FIG. 3A. The regions are selected automatically, without necessarily requiring additional manual input from the operator.

The size of each of the "holes" of the selected region(s) is equal to or larger than a sampling region used to perform the uniform sampling, for example, the size of each "hole" is larger than the size of a single cell of the 3D grid used to uniformly sample the location indications.

Optionally, the region is selected according to a location within the interior of the body cavity, away from an inner wall of the body cavity. Such region may be selected based on the rules that the inner wall, where the physician performs the medical procedure, should not be modified, but the interior of the body cavity, where no procedure is performed, may be modified to improve the reconstruction of the image of the body cavity.

Optionally, the region(s) is selected according to a predefined distance away from an estimated location indication of an inner wall of the body cavity. The predefined distance may represent a confidence interval such that location indications located a minimum of the predefined distance represent location indications of the interior of the body cavity and do not represent the tissue of the inner wall of the body cavity. The predefined distance helps in making sure that the location indications corresponding to anatomical locations of tissue of the inner wall of the body cavity are not tampered with.

The predefined distance away from the inner wall may be computed based on a predefined Mahalanobis distance from a computed center of mass of the uniformly sampled location indications. For example, a sphere or circle of a radius of the predefined Mahalanobis distance is drawn around the center of mass, where the selected region is defined as being enclosed within the sphere or circle. The predefined distance threshold is selected to exclude location indications corresponding to anatomical tissue of the inner wall of the body cavity from being included in the selected region.

Optionally, the region(s) are selected according to a prediction of cells of the 3D grid lacking location indications. The 3D grid is used for sampling the location indications to compute the uniformly sampled location indications, as described with reference to act 304 of FIG. 3A.

The region(s) may be selected, for example, according to anatomy and/or procedure being performed. The region(s) may be selected, for example, based on a template and/or an analysis of previous similar medical procedures performed at a similar anatomical location, where the analysis identifies region(s) lacking location indications. The region(s) may be selected, for example, by the operator via a GUI, which may list available anatomical locations and/or procedures.

As described herein, the region(s) including "holes" for computation of the emulated location indication(s) may be selected according to known anatomical structures. In an exemplary implementation, the body cavity is the left atrium. In such a case, the region(s) may be selected according to the following exemplary process. A first region corresponding to the middle portion of the left atrium is selected, by including points and/or locations having Mahalanobis distances from a center of mass of the uniformly sampled plurality of location indications less than a predefined distance threshold, for example, about 1.05, 1.1, 1.2, or other values. A second region corresponding to the bottom portion of the left atrium is selected, according to a set of rules different than the Mahalanobis distances for identifying the first region corresponding to the middle portion of the left atrium. The set of rules for selecting the second region corresponding to the bottom portion of the left atrium may include one or more of the following:

(i) Selecting points and/or location within a lower border of the second region defined according to a predefined height above a bottom of the location indications. The predefined height is selected to exclude indication locations denoting tissue of the inner wall of the body cavity, and/or to include indication locations denoting anatomical locations within the cavity itself (e.g., blood and/or other fluid within the body cavity).

(ii) A non-height dimension of the second region is the same as a corresponding non-height dimension of the first region, where the non-height dimension is for example, a width, a diameter.

(iii) An upper border of the second region penetrates the first region. The penetration of the first region by the second region is according to a predefined portion of location indications of the first region, for example, a predefined percentage of the location indications of the first region, for example, about 40%, or about 50%, or about 60%, or about 40%-60%, or other values.

The first region and the second region are unified to create the selected region, to which location indications may be added to emulate visits of the probe in additional locations in the first region.

Figure 5:
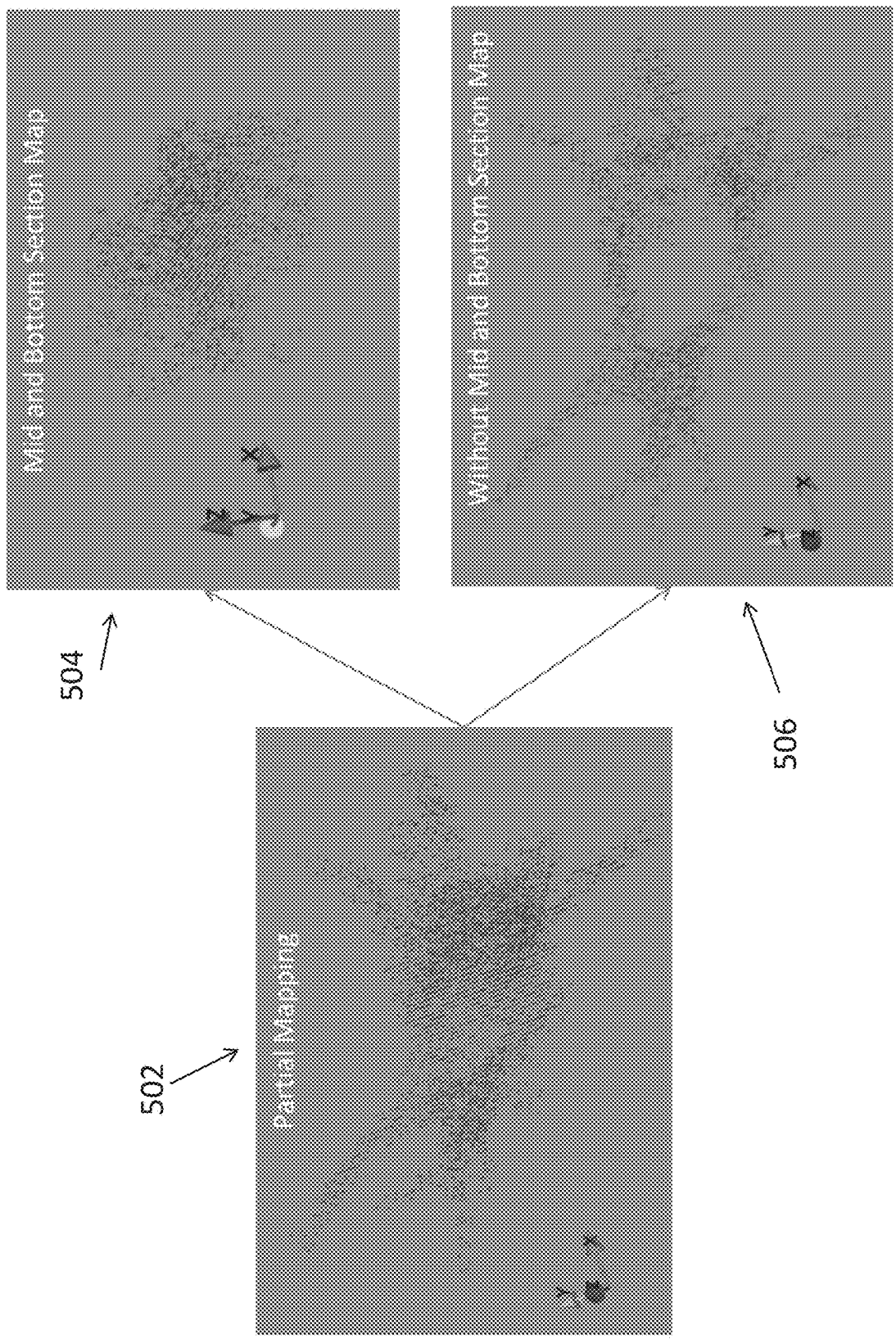
FIG. 5 is a schematic depicting an example of selecting the middle and bottom regions of the left atrium, in accordance with some embodiments of the present invention.

Reference is now made to FIG. 5, which is a schematic depicting an example of selecting the middle and bottom regions of the left atrium, in accordance with some embodiments of the present invention. Schematic 502 denotes the location indications received. Schematic 504 denotes the unified region created based on the identified middle and bottom portions of the left atrium. Schematic 506 denotes the portion of the location indications of schematic 502 excluding the unified region of schematic 504. The remaining location indications including the inner wall of the body cavity and location indications away from the wall, within the predefined distance threshold.

Referring now back to FIG. 3B, at 354, a set of emulated location indications within the selected region(s) is computed. The emulated location indications are designed to mimic actual location indications within the "holes" that may otherwise be obtained if the operator were to maneuver the sensor on the catheter to within the "holes", but the operator did not in fact obtain the location indications within the "holes". The emulated location indications improve reconstructions of the image of the body cavity, preventing tunnels, cavities, holes, and/or other discontinuities within the reconstructed image, as described herein.

Emulated location indications may be assigned to the certain group corresponding to the respective selected region.

As used herein, the term non-emulated location indications refers to the location indications computed based on the received data, as described with reference to act 302, rather than the emulated location indications, added to the non-emulated location indications to represent pseudo location indications not based on the received data, but rather generated by the reconstruction process to emulate additional visits of the probe.

Optionally, the set of emulated location indications are computed by computing another PDF for the selected region. The PDF for the selected region may be based on the PDF computed for the non-emulated location indications described with reference to act 306.

The PDF for the selected region may be different than the PDF computed for the non-emulated location indications. Another 3D grid of cells may be computed for the selected region(s). The 3D grid of cells computed for the selected region(s) may include the same size of cells as the 3D grid of cells computed for the non-emulated location indications as described with reference to act 306, or the 3D grid of cells may include different sized cells. One or more emulated location indication is computed for each cell of the 3D grid, wherein the PDF is above a predetermined threshold. This threshold is lower than the one used in act 308. This lower threshold causes places that were empty before, to be filled with emulated location indications.

Figure 6:
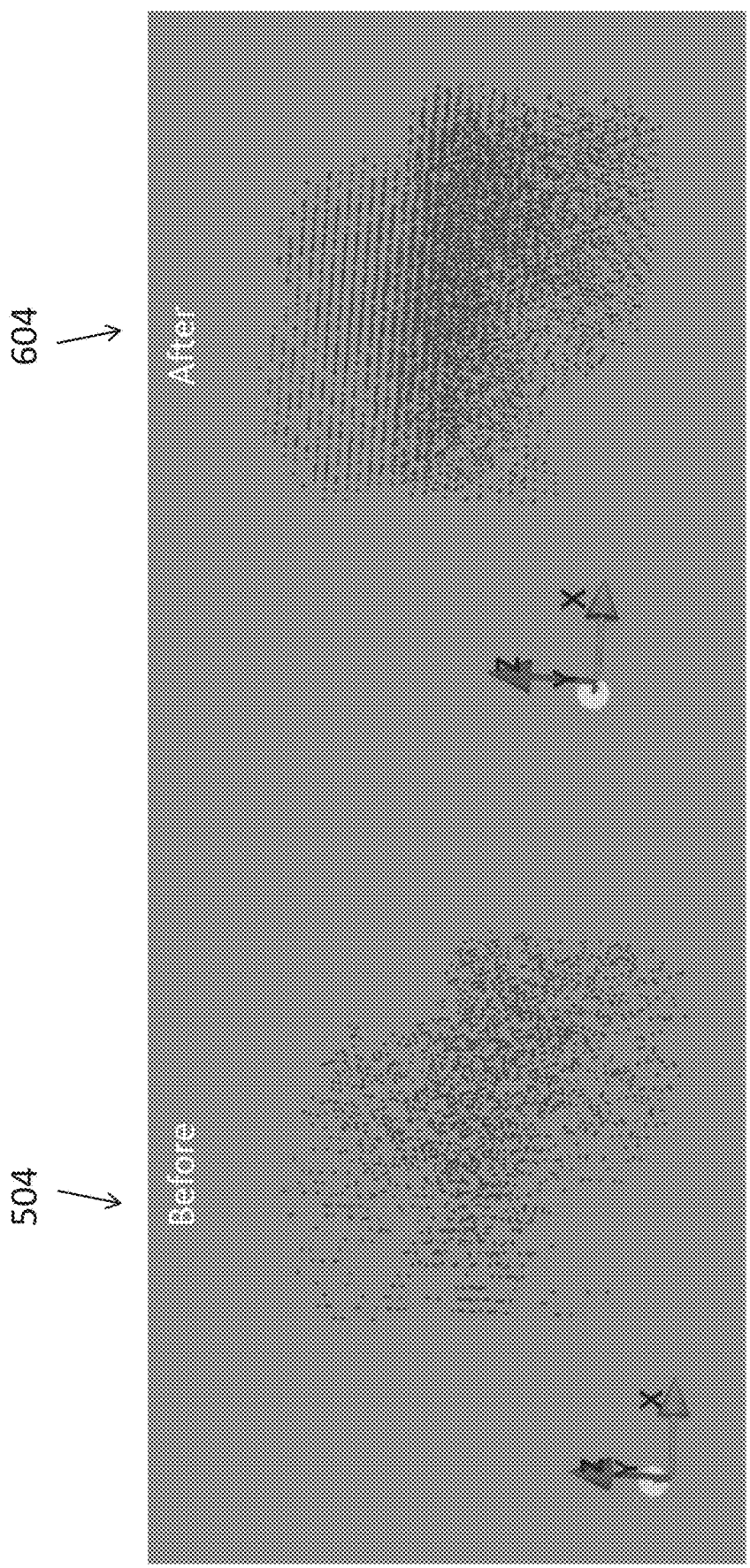
FIG. 6 is a schematic depicting the unified region of the left atrium without emulated location indications, and the same unified region of the left atrium including the computed emulated location indications, in accordance with some embodiments of the present invention.

Reference is now made to FIG. 6, which is a schematic depicting the unified region of the left atrium 504 without emulated location indications as shown in FIG. 5, and the same unified region of the left atrium including the computed emulated location indications 604, in accordance with some embodiments of the present invention. It is noted that region 504 without emulated location indications appears to have large "holes" without any location indications, in comparison to region 604 where such large "holes" have been filled with emulated location indications, as described herein. Filling of the "holes" with the emulated location indications improves accuracy of the reconstructed image, as described herein.

Figure 7:
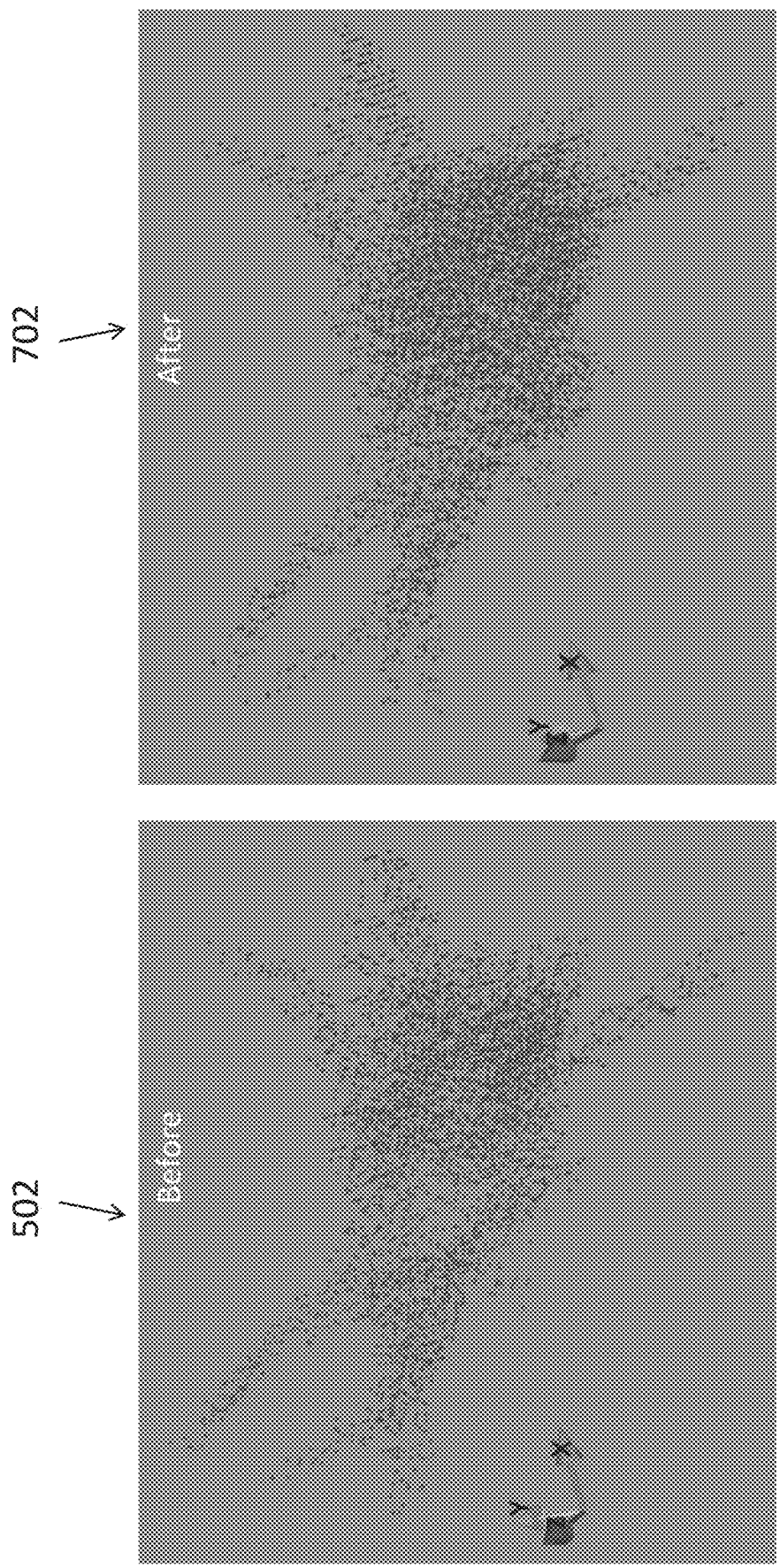
FIG. 7 is a schematic depicting the location indications of the left atrium without emulated location indications and the same left atrium including the computed emulated location indications, in accordance with some embodiments of the present invention.

Reference is now made to FIG. 7, which is a schematic depicting the location indications of the left atrium 502 without emulated location indications as shown in FIG. 5, and the same left atrium including the computed emulated location indications 702, in accordance with some embodiments of the present invention. Left atrium including the computed emulated location indications 702 is created by merging non-emulated location indications 506 as shown in FIG. 5 with the unified region of the left atrium including the computed emulated location indications 604 as shown in FIG. 6. It is noted that region 504 without emulated location indications appears to have large "holes" without any location indications, in comparison to region 702 where such large "holes" have been filled with emulated location indications, as described herein. Filling of the "holes" with the emulated location indications improves accuracy of the reconstructed image, as described herein.

Referring now back to FIG. 3B, at 356, the set of emulated location indications and the non-emulated location indications are uniformly sampled. The uniform sampling is performed as described with reference to act 304 of FIG. 3A. It is noted that the emulated location indications may be added before the uniform sampling. Alternatively, when the uniform sampling of the non-emulated location indications has been previously performed with reference to act 352, where the region(s) is selected from the uniformly sampled non-emulated location indications, the uniform sampling is performed for the emulated location indications.

At 358, the PDF is computed based on the uniformly sampled non-emulated location indications and the uniformly sampled set of emulated location indications. The PDF is computed as described with reference to act 306 of FIG. 3A.

At 360, the contour function is computed as described with reference to act 308 of FIG. 3A. In some embodiments, the method may end here, by providing the image reconstructed from the contour function using, e.g., marching cube or pivoting ball algorithm, for example, implementing 364 without 362. In some embodiments, the method may further include markings of ablation points, or other regions their location is identified in higher confidence than the locations of other location indications, for example, as described with reference to 362.

Accordingly, at 362, one or more markings indicative of an anatomical location of the body cavity where a medical procedure is performed is provided. The markings may be indicative of, for example, lesions ablated in an ablation procedure. The markings may be provided, for example, based on output of a sensor on the intra body probe that performed the ablation or associated with an ablation element that senses the performed ablation.

Optionally, one or more of the location indications denote the procedure marking, for example, when the location indications correspond to the treatment element performing the procedure, for example, to an electrode performing an ablation procedure. The marking may be automatically determined, for example, by code that detects when treatment is being performed, and tags the real time location indications as procedure markings. Alternatively or additionally, the marking may be manually determined, for example, by a user manually indicating when the treatment is occurring and/or manually tagging a current location as a treatment location, for example, via a graphical user interface that presents the reconstructed image.

At 364, the image of the body cavity is reconstructed as described with reference to act 310 of FIG. 3A.

Optionally, when procedure markings as described with reference to act 362 are provided, markings having an actual location greater than a predefined outlier distance from the mesh are excluded from the image of the outer shell. Such markings may represent errors in measurement and/or errors in their location, due to their being located at an unexpected location away from target tissue.

Optionally, when procedure markings as described with reference to act 362 are provided, the original actual location corresponding to each marking is maintained. The image of the outer shell of the body cavity is reconstructed according to the contour function and the marking(s) by computing a mesh denoting the outer shell to intersect each of the marking(s) at their original actual location.

Reference now back to FIG. 8, schematic 802 depicts a reconstruction of a left atrium including procedure markings denoting location of ablations in a left atrium before correction as described herein. Schematic 804 depicts a reconstruction of the left atrium including correction based on procedure markings denoting location of ablations in a left atrium created in accordance with some embodiments of the present invention. It is noted that in schematic 802, the left atrium may be reconstructed as described herein. Ablation markings appear slightly above or below the reconstructed shell of the left atrium, for example, ablation marking 806 is shown elevated above the surface of the left atrium. The location of ablation marking 806 represents a trust-worthy point since the catheter spent a significant amount of time at the corresponding physical location performing the ablation. The free floating appearance of marking 806 in schematic 802, which is a trust-worthy point, is selected for correction of the reconstructed shell. In schematic 804 the shell of the left atrium is corrected to intersect the trust-worthy ablation markings 806 at the surface of the left atrium. In the correction, ablation marking 806 appears on the surface of the left atrium, rather than free floating above the surface, representing the actual physical location of ablation corresponding to marking 806.

Referring now back to FIG. 3B, at 366, the reconstructed image is provided, for example, presented on a display, as described with reference to act 312 of FIG. 3A.

At 368, acts 350-366 are iterated for updating the reconstructed image of the outer shell of the body cavity, as described with reference to act 314 of FIG. 3A.

Figure 9:
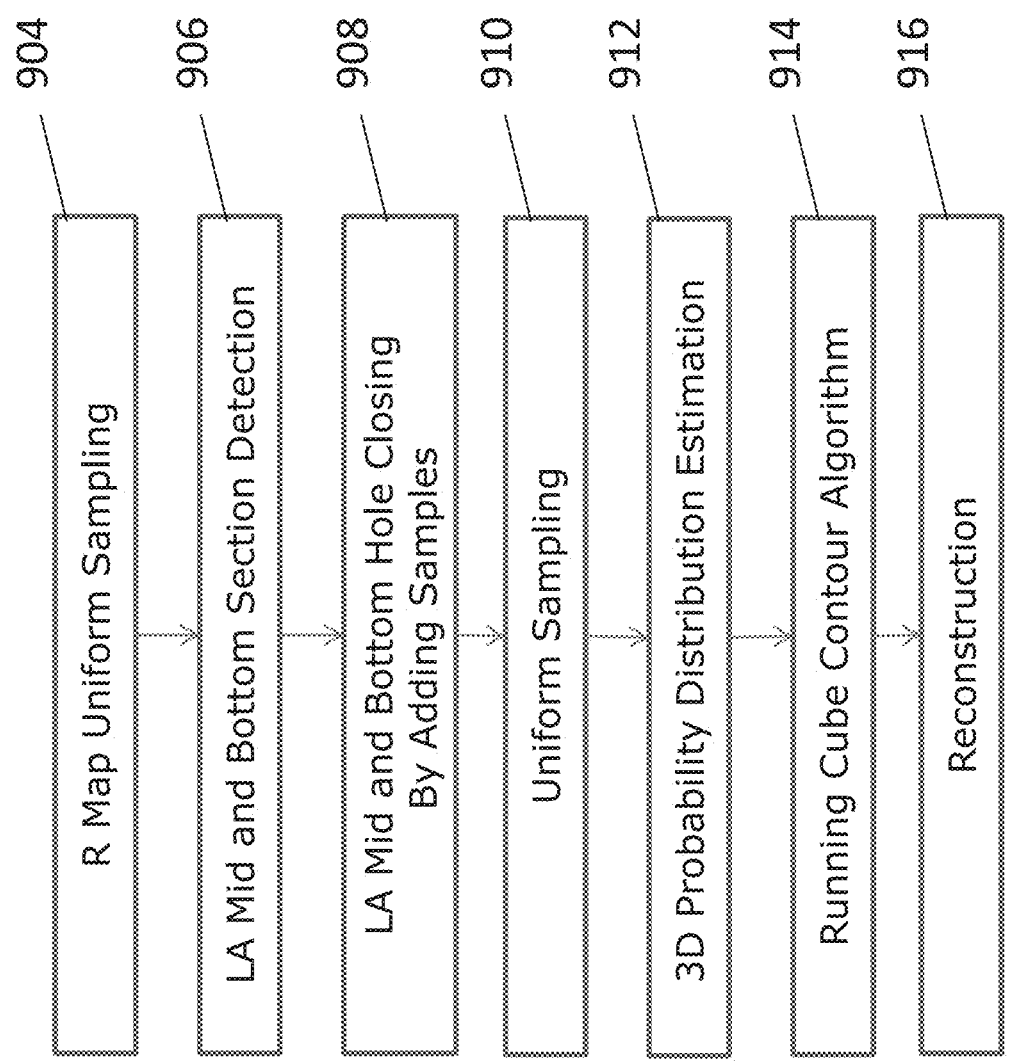
FIG. 9 is a flowchart of an exemplary method for reconstructing an image of a shell of the left atrium based on location indications, in accordance with some embodiments of the present invention.

Reference is now made to FIG. 9, which is a flowchart of an exemplary method for reconstructing an image of a shell of the left atrium based on location indications, in accordance with some embodiments of the present invention. The method described with reference to FIG. 9 is based on an exemplary implementation of the methods described with reference to FIGS. 3A-3B. The method described with reference to FIG. 9 is implementable by components of system 400 described with reference to FIG. 4, optionally by processor(s) 404 of computing device 402 executing code 406A. Code 406A may store instructions for implementing the acts and/or features of the method described with reference to FIG. 9.

At 904, the location indications are uniformly sampled, for example, as described with reference to act 304 of FIG. 3A.

At 906, the middle and bottom regions of the left atrium which are expected to include "holes" are detected, for example, as described with reference to act 352 of FIG. 3B.

At 908, the "holes" in the middle and bottom regions are closed by computing emulated location indications, for example, as described with reference to act 354 of FIG. 3B.

At 910, the emulated location indications and optionally the non-emulated location indications are uniformly sampled, for example, as described with reference to act 304 of FIG. 3A and/or act 356 of FIG. 3B.

At 912, the PDF is computed based on the uniformly sampled emulated location indications and the non-emulated location indications, for example, as described with reference to act 306 of FIG. 3A and/or act 358 of FIG. 3B.

At 914, the contour function is computed based on the PDF, for example, according to the running cube contour process, as described with reference to act 308 of FIG. 3A and/or act 360 of FIG. 3B.

At 916, the image of the left atrium is reconstructed based on the contour function, for example, as described with reference to act 310 of FIG. 3A and/or act 364 of FIG. 3B.

An exemplary image of the left atrium computed based on the method described with reference to FIG. 9 is shown as left atrium 202 of FIG. 2.

Figure 10:
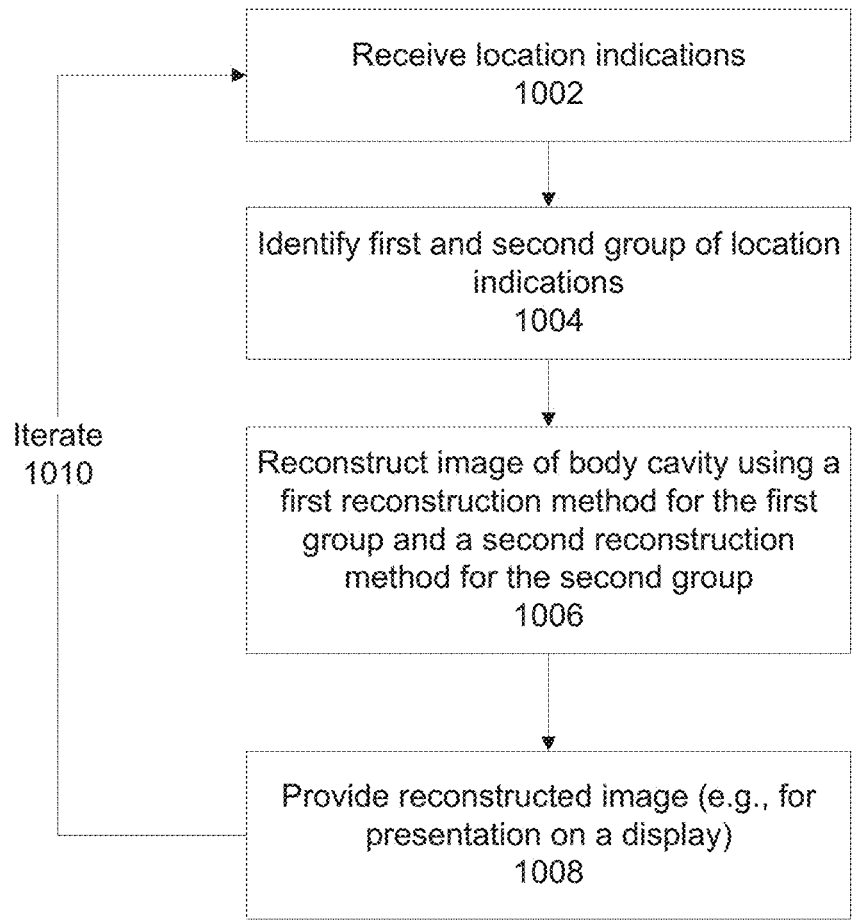
FIG. 10 is a flowchart of a process of reconstructing an image of a body cavity shape of a subject based on location indications of sensor(s) disposed on an intrabody probe within the body cavity, in accordance with some embodiments of the present invention.

Reference is now made to FIG. 10, which is a flowchart of an exemplary process of reconstructing an image of a body cavity shape of a subject based on location indications of sensor(s) disposed on an intrabody probe within the body cavity, in accordance with some embodiments of the present invention. The process is based on dividing the location indications into at least two groups, e.g., each group of location indications indicating locations in a different region of the body cavity, and reconstructing each group using a different approach and/or using different reconstructions parameters. Acts and/or features of the method described with reference to FIG. 10 may be based on and/or correspond to one or more acts and/or features of the method described with reference to FIGS. 3A and/or 3B. The acts and/or features of the method described with reference to FIG. 10 may be implemented by components of system 400 described with reference to FIG. 4, optionally by processor(s) 404 of computing device 402 executing code 406A. Code 406A may store instructions for implementing the acts and/or features of the method described with reference to FIG. 10.

At 1002, data indicative of location indications of the sensor(s) disposed on the intrabody probe within the body cavity is received, for example, as described with reference to act 302 described with reference to FIG. 3A and/or act 350 described with reference to FIG. 3B.

At 1004, at least a first group and a second group of location indications are identified based on the data indicative of location indications of the sensor(s). The locations indicated by the location indications of each group indicate locations in a different region of the body cavity. The first and second group of location indications are optionally identified according to proximity of the indicated locations to an outer shell of the body cavity. The locations indicated by the location indications of the first group are closer to the outer shell of the body cavity than the locations indicated by the location indications of the second group, or vice versa. Alternatively, the first and second group of location indications may be identified according to proximity of the indicated locations to a center of mass of the locations indicated by the location indications. For example, location indications indicating locations near the center of mass may make part of the second group (corresponding to an inner region), and location indications indicating locations further from the center of mass may make part of the first group (corresponding to an outer region). The terms "further" and "closer" may be defined in this context as larger or shorter than a predefined distance, respectively.

In one example, the first group represent a target region where a medical procedure is likely to be performed, for example, target tissue of the inner wall of the body cavity that is likely to be ablated by an ablation catheter in an ablation procedure. The second group represents the remaining portion of the body cavity where no medical procedure is likely to be performed. In another example, both the first and second group represent anatomical regions where no medical procedure is likely to be performed, for example, the interior of the body cavity. However, the first region, which includes location indications closer to the inner wall of the body cavity, may likely include some target tissue and/or may include a higher density of location indications in comparison to the second region located closer towards the center of the cavity. Since the catheter is expected to reside longer and/or visit a greater number of anatomical locations along the inner wall of the body cavity, the density of location indications in the first region is expected to be higher than the density of location indications in the second region.

In some embodiments, the second group may correspond to the selected region(s) described with reference to act 352 of FIG. 3B. In other embodiments, both the first and second group correspond to the selected region(s) described with reference to act 352 of FIG. 3B.

At 1006, an image of the body cavity is reconstructed from the data indicative of location indications of the sensor(s). The image is reconstructed, using a first reconstruction method for the first group of location indications, and a second reconstruction method for the second group of location indications.

Optionally, each of the first and second reconstruction methods includes uniformly sampling the data in the corresponding group, for example, as described with reference to act 304 described with reference to FIG. 3A and/or act 356 described with reference to FIG. 3B.

Optionally, each of the first and second reconstruction methods includes setting a threshold to the point density function describing the density of the location indications in the corresponding group. Each of the point density functions describes the density of the uniform sample of location indications of the respective group. The two methods differ in the value of the threshold. The threshold for the second group, which in some embodiments is expected to include location indications known to be within the interior of the body cavity, away from the inner wall targeted for therapeutic treatment, is set differently than the threshold for the first group which is expected to include location indications corresponding to target tissue likely to be treated. For example, the threshold for the second group is set lower than the threshold for the first group based on the increased likelihood of location indications of the second group corresponding to actual anatomical locations away from the target tissue of the wall of the body cavity.

In some embodiments, a first group of location indications contains more location indications than a second group of location indications. In some embodiments, the first group includes location indications indicating location that are closer to the inner wall than locations indicated by the location indications of the second group. In such embodiments, the reconstruction method applied to the first group of location indicators (i.e., the group of the outer ones) comprises emulating a smaller number of location indications than the reconstructions method applied to the second group of location indications. In some embodiments, no location indications are emulated for the first group. Location indications that may be "missing" from the first group, for example, of the outer shell of the interior of the body cavity, may appear to miss due to the structure of the shell, for example, that makes it difficult for the sensor to visit certain regions of the interior of the body cavity. The second group, which may represent the interior of the body cavity, may be pre-known to be a blood pool (e.g., without holes and tubes in it) where the catheter does not necessarily visit or visits less often, since the blood pool is not interesting in terms of treatment, for example, no ablation tissue exists there. Optionally, the two methods differ in the density of emulated location indicators per group, or in the absolute number of the emulated location indicators per group. In some embodiments, they differ both in number and in density per group. For example, the density of emulated location indications may be higher for one group in regions where the received data were less dense, e.g., away from the outer shell, than for another group in regions where the received data was denser. In some embodiments, the density of location indicators, genuine and emulated together, may be substantially the same for the two groups taken from the two regions. In the present disclosure and claims, substantially the same means differ by no more than 10%. Thus, in some embodiments, the first reconstruction method comprises emulating a first non-zero number of location indications, and the second reconstruction method comprises emulating a second number of location indications, the second number being larger than the first number. Such implementation may be used, for example, when the second group is closer to the center of the body cavity and the first group is closer to the inner wall of the body cavity.

The working assumption is that more location indications are obtained closer to the inner wall than within the interior of the body cavity. In such implementation, both the first and second group may be corresponding to the selection region(s) described with reference to act 352 of FIG. 3B.

Alternatively, the first reconstruction method includes the process of emulating location indications, and the second reconstruction method does not include the process of computing emulated location indications. Such implementation may be used, for example, when the first group is likely to include the inner wall and the second group is likely to include the interior of the body cavity. The working assumption is that the first group should not be tampered with since it includes actual target tissue while the second group may be adapted to improve reconstruction of the image. In such implementation, the second group may correspond to the selection region(s) described with reference to act 352 of FIG. 3B, which the first group corresponds to the non-emulated location indications described herein.

Additional details of setting the threshold of the PDF, computing the PDF, computing the contour function based on the PDF, and reconstructing the image are for example, described herein with reference to acts 306-310 of FIG. 3A and/or acts 358-364 of FIG. 3B.

At 1008, the reconstructed image is provided, optionally for presentation on a display, for example, as described with reference to act 312 described with reference to FIG. 3A and/or act 366 described with reference to FIG. 3B.

At 1010, acts 1002-1008 are iterated for dynamically updating the reconstructed image when additional data indicative of location indications is received, for example, when the catheter is maneuvered to additional locations within the body cavity.

Figure 11:
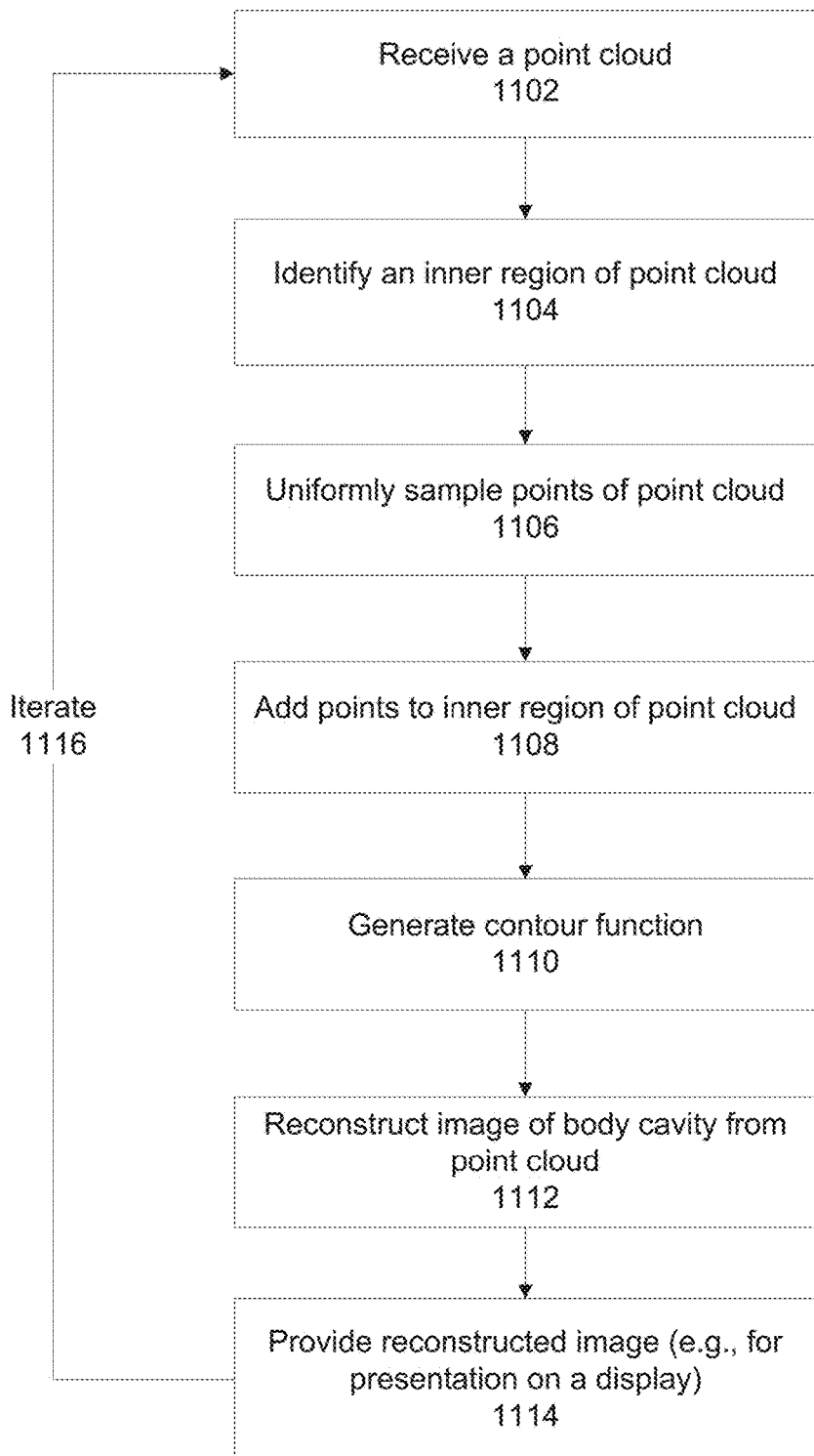
FIG. 11 is a flowchart of a process of reconstructing an image of a body cavity shape of a subject based on a point cloud, in accordance with some embodiments of the present invention.

Reference is now made to FIG. 11, which is a flowchart of a process of reconstructing an image of a body cavity shape of a subject based on a point cloud, in accordance with some embodiments of the present invention. Each point of the point cloud represents a location visited by the intra body probe described herein, and is therefore equivalent to a location indication. The location visited by the intra body probe may represent locations visited by the sensor(s) located on the intra body probe, as described herein. The point cloud has an inner region where the points are sparser than outside the inner region, for example, the point cloud may represent a cavity in the body such as a heart chamber, where the intra body probe tends to be navigate along the inner walls of the cavity in order to map the cavity and/or determine the location of tissue for treatment (e.g., ablation), more than within the blood pool (or pool of other fluid) located in the interior of the chamber. It is noted that there may be two or more inner regions where points are sparser than outside the inner regions.

Acts and/or features of the method described with reference to FIG. 11 may be based on and/or correspond to one or more acts and/or features of the method described with reference to FIGS. 3A and/or 3B and/or 10. The acts and/or features of the method described with reference to FIG. 11 may be implemented by components of system 400 described with reference to FIG. 4, optionally by processor(s) 404 of computing device 402 executing code 406A. Code 406A may store instructions for implementing the acts and/or features of the method described with reference to FIG. 11.

At 1102, a point cloud is received. The point cloud or portions thereof may be received as individual points that are sequentially received such as when each point is received as it is measured, or as a set of points, received after multiple points have been measured. Each point of the point cloud represents a location visited by the sensor(s) disposed on the intrabody probe within the body cavity, for example, as described with reference to act 302 described with reference to FIG. 3A and/or act 350 described with reference to FIG. 3B.

At 1104, the inner region of the point cloud is identified. In some embodiments, the inner region may be identified as the region lying a predefined distance away from an estimated location of an inner wall of the body cavity. In some such embodiments, the inner region may include points of the point cloud that are located at a distance equal to or greater than a predetermined distance away from the estimated location of the inner wall of the body cavity. Alternatively, the inner region may be identified as the region lying a predefined distance from a center of mass of the point cloud. In some such embodiments, the inner region may include points of the point cloud location at a distance equal to or smaller than a predetermined distance from a center of mass of the point cloud.

The point cloud may include two groups of points. The first group corresponds to the inner region, and includes the points of the point cloud located in the inner region. The second group includes the points of the point cloud that are not located in the inner region. The second group corresponds to the region lying less than the predefined distance away from the estimated location of the inner wall of the body cavity, which may be referred to as an outer region.

It is noted that the point cloud may include more than two groups that correspond to multiple inner regions.

Additional exemplary processes for identifying the first and second groups of point clouds are described, for example, with reference to act 1004 of FIG. 10.

At 1106, the points in the point cloud are uniformly sampled, for example, as described with reference to act 304 described with reference to FIG. 3A and/or act 356 described with reference to FIG. 3B. In some embodiments, 1106 may be skipped, and the method may proceed from 1104 directly to 1108.

At 1108, points are added to the inner region of the point cloud. The points are added to emulate additional visits of the intrabody probe in the inner region. In some embodiments, the process of adding the points is carried out after the process of uniform sampling as described with reference to act 1106. The emulated points may be computed and added, for example, as described with reference to act 354 described with reference to FIG. 3B. Optionally, both original and added (i.e., non emulated and emulated) are uniformly sampled before continuing to 1110. The uniform sampling may be carried out as described with reference to act 304 described with reference to FIG. 3A and/or act 356 described with reference to FIG. 3B.

At 1110, a contour function is generated. The contour function is generated by computing a point density function (PDF) based on the uniformly sampled point cloud, and subtracting a predetermined threshold from the computed PDF.

The PDF may be computed, for example, as described with reference to act 306 described with reference to FIG. 3A and/or act 358 described with reference to FIG. 3B. The contour function may be computed, for example, as described with reference to act 308 described with reference to FIG. 3A and/or act 360 described with reference to FIG. 3B.

At 1112, the image of the body cavity shape is reconstructed from the point cloud after the adding of the points as described with reference to act 1108. The reconstructing is based on the contour function, computed as described with reference to act 1110.

An outer shell of the shape may be reconstructed according to locations where the contour function borders between positive and negative values.

The outer shell of the shape may be reconstructed from the contour function, for example, according to a marching cube computational process.

The image may be reconstructed, for example, as described with reference to act 310 described with reference to FIG. 3A and/or act 364 described with reference to FIG. 3B and/or act 1006 described with reference to FIG. 10.

At 1114, the reconstructed image is provided, for example, for presentation on a display, for example, as described with reference to act 312 described with reference to FIG. 3A and/or act 366 described with reference to FIG. 3B and/or act 1008 described with reference to FIG. 10.

At 1116, acts 1102-1114 are iterated for dynamically updating the reconstructed image when additional points of the point cloud are received, for example, when the intra body probe is maneuvered to additional locations within the body cavity.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant location indications will be developed and the scope of the term location indication is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of reconstructing an image of a body cavity shape of a subject based on a point cloud, each point representing a location visited by an intra-body probe, the point cloud having an inner region wherein the points are sparser than outside said inner region of the point cloud, the method comprising:

uniformly sampling the points in the point cloud;
identifying the inner region;
after said uniformly sampling, adding points to the inner region of the cloud to emulate additional visits of the intrabody probe in said inner region; and
reconstructing the image of the body cavity shape from the point cloud after the adding;
wherein said reconstructing is based on a contour function generated by:
computing a point density function (PDF) based on the uniformly sampled point cloud, and
computing the contour function by subtracting a predetermined threshold from the computed PDF.

2. The method of claim 1, wherein said reconstructing comprises reconstructing an outer shell of the shape according to locations wherein the contour function borders between positive and negative values.

3. The method of claim 1, wherein said reconstructing comprises reconstructing an outer shell of the shape from the contour function according to a marching cube computational process.

4. The method of claim 1, comprising identifying the inner region as a region lying a predefined distance away from an estimated location of an inner wall of the body cavity.

5. A system for reconstructing an image of a body cavity shape of a subject based on a point cloud, in which each point represents a location visited by an intra-body probe, the point cloud having an inner region wherein the points are sparser than outside said inner region, the system comprising a non-transitory memory having stored thereon a code for execution by at least one hardware processor, the code comprising:

code for uniformly sampling the points in the point cloud;
code to add points to the inner region of the cloud to emulate additional visits of the intrabody probe in said inner region, wherein said code to add points is executed after said uniformly sampling; and
code to reconstruct the image of the body cavity shape from the point cloud after the adding;
wherein the code to reconstruct the image comprises code to evaluate a contour function generated by:
computing a point density function (PDF) based on the uniformly sampled point cloud, and
computing the contour function by subtracting a predetermined threshold from the computed PDF.

6. The system of claim 5, wherein said code for reconstructing comprises code for reconstructing an outer shell of the shape according to locations wherein the contour function borders between positive and negative values.

7. The system of claim 5, wherein said code for reconstructing comprises code for reconstructing an outer shell of the shape from the contour function according to a marching cube computational process.

8. The system of claim 5, wherein the instructions further comprise code for identifying the inner region as a region lying a predefined distance away from an estimated location of an inner wall of the body cavity.

* * * * *